(12) United States Patent
Keller et al.

(10) Patent No.: US 11,712,502 B2
(45) Date of Patent: Aug. 1, 2023

(54) SYSTEMS, DEVICES, AND METHODS FOR EXTRACORPOREAL REMOVAL OF CARBON DIOXIDE

(71) Applicants: Steven Paul Keller, Brookline, MA (US); Brian Yale Chang, Boston, MA (US); Jayon Wang, Allston, MA (US)

(72) Inventors: Steven Paul Keller, Brookline, MA (US); Brian Yale Chang, Boston, MA (US); Jayon Wang, Allston, MA (US)

(73) Assignees: Steven Paul Keller, Brookline, MA (US); Brian Yale Chang, Boston, MA (US); Jayon Wang, Allston, MA (US)

( * ) Notice: Subject to any disclaimer, the term of this patent is extended or adjusted under 35 U.S.C. 154(b) by 393 days.

(21) Appl. No.: 16/647,942

(22) PCT Filed: Sep. 17, 2018

(86) PCT No.: PCT/US2018/051370
§ 371 (c)(1),
(2) Date: Mar. 17, 2020

(87) PCT Pub. No.: WO2019/055933
PCT Pub. Date: Mar. 21, 2019

(65) Prior Publication Data
US 2020/0261635 A1    Aug. 20, 2020

Related U.S. Application Data

(60) Provisional application No. 62/559,583, filed on Sep. 17, 2017.

(51) Int. Cl.
*A61M 1/16* (2006.01)
*B01D 19/00* (2006.01)

(52) U.S. Cl.
CPC ........ *A61M 1/1647* (2014.02); *A61M 1/1627* (2014.02); *B01D 19/0031* (2013.01);
(Continued)

(58) Field of Classification Search
CPC .............. A61M 1/1647; A61M 1/1627; A61M 2202/0225; A61M 2230/208;
(Continued)

(56) References Cited

U.S. PATENT DOCUMENTS 5,866,015 A    2/1999  Krämer
6,271,023 B1*  8/2001  Baurmeister ........ B01D 63/026
                                                  210/321.64
(Continued)

FOREIGN PATENT DOCUMENTS

EP    2150291 B1    8/2011
EP    2712639 A1    4/2014
(Continued)

OTHER PUBLICATIONS

International Search Report & Written Opinion PCT Application No. PCT/US18/51370, dated Feb. 27, 2019, 16 pages.
(Continued)

*Primary Examiner* — Krishnan S Menon
(74) *Attorney, Agent, or Firm* — Morgan, Lewis & Bockius LLP

(57) ABSTRACT

Systems, devices, and methods are provided for removing carbon dioxide from a target fluid, such as, for example, blood, to treat hypercarbic respiratory failure or another condition. A device is provided including first and second membrane components for removing dissolved gaseous carbon dioxide and bicarbonate from the fluid, which can be done simultaneously. The device can be in the form of a cartridge configured for use in a dialysis system. A method of treatment is also provided, involving drawing blood from (Continued)

a patient and bringing the patient's blood in contact with a first membrane component having a sweep gas passing therethrough, and a second membrane component having a dialysate passing therethrough. The dialysate's composition can be selected such that charge neutrality is maintained.

18 Claims, 15 Drawing Sheets

(52) U.S. Cl.
CPC .............. *A61M 2202/0225* (2013.01); *A61M 2230/208* (2013.01)

(58) Field of Classification Search
CPC .............. A61M 1/1605; A61M 1/1623; A61M 1/1633; A61M 1/3666; A61M 1/1698; B01D 19/0031; B01D 2311/13; B01D 2311/14; B01D 2311/24; B01D 2313/08; B01D 2319/06; B01D 61/243; B01D 61/28; B01D 61/32; B01D 63/02; Y02C 20/40
See application file for complete search history.

(56) References Cited

U.S. PATENT DOCUMENTS

| | | |
|---|---|---|
| 6,623,443 B1 | 9/2003 | Polaschegg |
| 7,674,236 B2 | 3/2010 | Daniel et al. |
| 7,763,097 B2 | 7/2010 | Federspiel et al. |
| 7,847,564 B2 | 12/2010 | Rossi |
| 7,927,544 B2 | 4/2011 | Federspiel et al. |
| 7,935,071 B2 | 5/2011 | Levin et al. |
| 8,034,161 B2 | 10/2011 | Gura et al. |
| 8,226,564 B2 | 7/2012 | Gencarelli |
| 8,292,851 B2 | 10/2012 | Ferrari |
| 8,323,379 B2 | 12/2012 | Federspiel et al. |
| 8,449,563 B2 | 5/2013 | Rebuffat et al. |
| 8,518,259 B2 | 8/2013 | Cloutier et al. |
| 8,603,021 B2 | 12/2013 | Levin et al. |
| 8,647,569 B1 | 2/2014 | Federspiel et al. |
| 8,668,825 B2 | 3/2014 | Pouchoulin et al. |
| 8,734,375 B2 | 5/2014 | Pesenti et al. |
| 8,795,591 B2 | 8/2014 | Roller et al. |
| 9,031,657 B2 | 5/2015 | Cristiani et al. |
| 9,050,420 B2 | 6/2015 | Zhang |
| 9,311,448 B2 | 4/2016 | Gruendken et al. |
| 9,375,525 B2 | 6/2016 | Greenberg et al. |
| 9,440,018 B2 | 9/2016 | Levin et al. |
| 9,750,865 B2 | 9/2017 | Vasta et al. |
| 9,770,546 B2 | 9/2017 | Vasta |
| 9,814,821 B2 | 11/2017 | Federspiel et al. |
| 9,831,709 B2 | 11/2017 | Romanelli et al. |
| 10,016,551 B2 | 7/2018 | Hersenius |
| 10,080,834 B2 | 9/2018 | Federspiel et al. |
| 10,098,993 B2 | 10/2018 | Meyer et al. |
| 10,195,327 B2 | 2/2019 | Meyer et al. |
| 10,201,646 B2 | 2/2019 | Peters et al. |
| 2007/0004023 A1 | 1/2007 | Trachtenberg |
| 2012/0040429 A1 | 2/2012 | Federspiel et al. |
| 2012/0152744 A1 | 6/2012 | Eisaman et al. |
| 2012/0190103 A1* | 7/2012 | Maurer .................. A61M 1/16 435/283.1 |
| 2012/0258545 A1 | 10/2012 | Ash et al. |
| 2014/0158588 A1 | 6/2014 | Pudil et al. |
| 2014/0299545 A1 | 10/2014 | Wrazel et al. |
| 2015/0122712 A1* | 5/2015 | Brandl ................ A61M 1/3612 210/96.2 |
| 2015/0335807 A1 | 11/2015 | Kellum, Jr. et al. |
| 2017/0100531 A1 | 4/2017 | Madhani et al. |
| 2018/0185567 A1 | 7/2018 | Madhani et al. |
| 2018/0243494 A1 | 8/2018 | Meyer et al. |
| 2018/0264184 A1 | 9/2018 | Jeffries et al. |
| 2019/0015574 A1 | 1/2019 | Kreymann et al. |

FOREIGN PATENT DOCUMENTS

| | | |
|---|---|---|
| EP | 2519279 B1 | 4/2015 |
| EP | 2689791 B1 | 4/2015 |
| EP | 2533827 B1 | 9/2015 |
| EP | 2667908 B1 | 6/2016 |
| EP | 2861272 B1 | 8/2017 |
| EP | 3174572 B1 | 9/2018 |
| EP | 2560746 B1 | 11/2018 |
| EP | 3237035 B1 | 1/2019 |
| WO | WO 2013/122749 A1 | 8/2013 |
| WO | WO 2016/177476 A1 | 11/2016 |
| WO | WO 2017/068081 A1 | 4/2017 |
| WO | WO 2018/109070 A1 | 6/2018 |
| WO | WO 2018/189142 A1 | 10/2018 |

OTHER PUBLICATIONS

Alessandri, et al., "Intermittent extracorporeal $CO_2$ removal in chronic obstructive pulmonary disease patients: a fiction or an option," Curr. Opin. Crit. Care, vol. 24, pp. 29-34, 2018.

Cove, et al., "Bench to bedside review: Extracorporeal carbon dioxide removal, past present and future," Critical Care, 16:203, 9 pages, 2012.

May, et al., "Extracorporeal $CO_2$ removal by hemodialysis: in vitro model and feasibility," Intensive Care Medicine Experimental, 5:20, 9 pages, 2017.

* cited by examiner

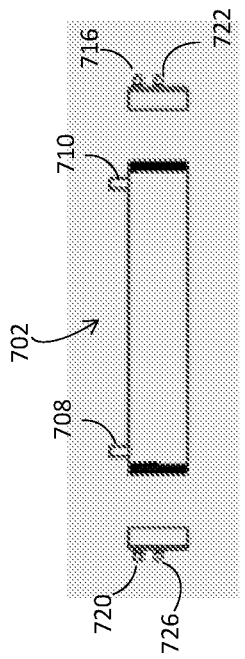
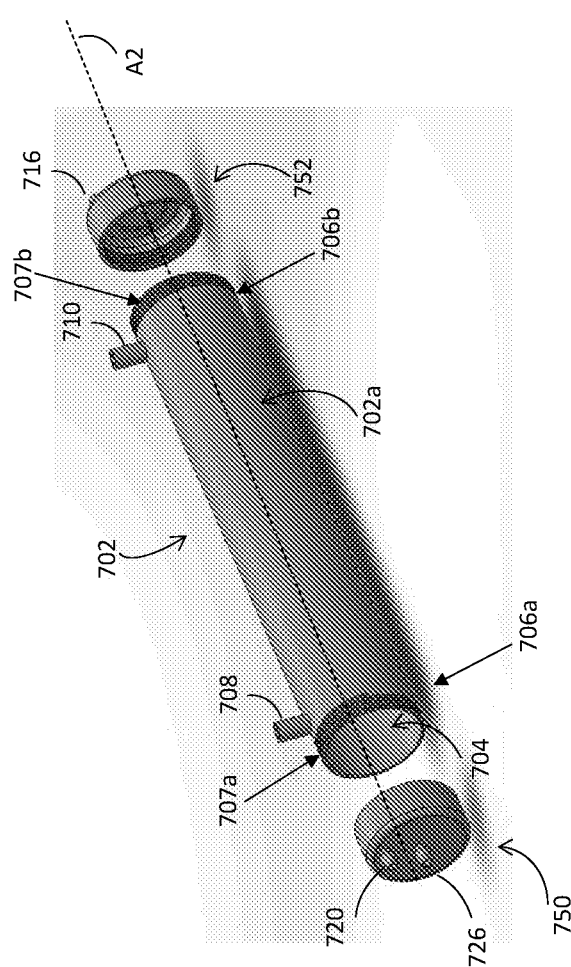
FIG. 7B
FIG. 7A

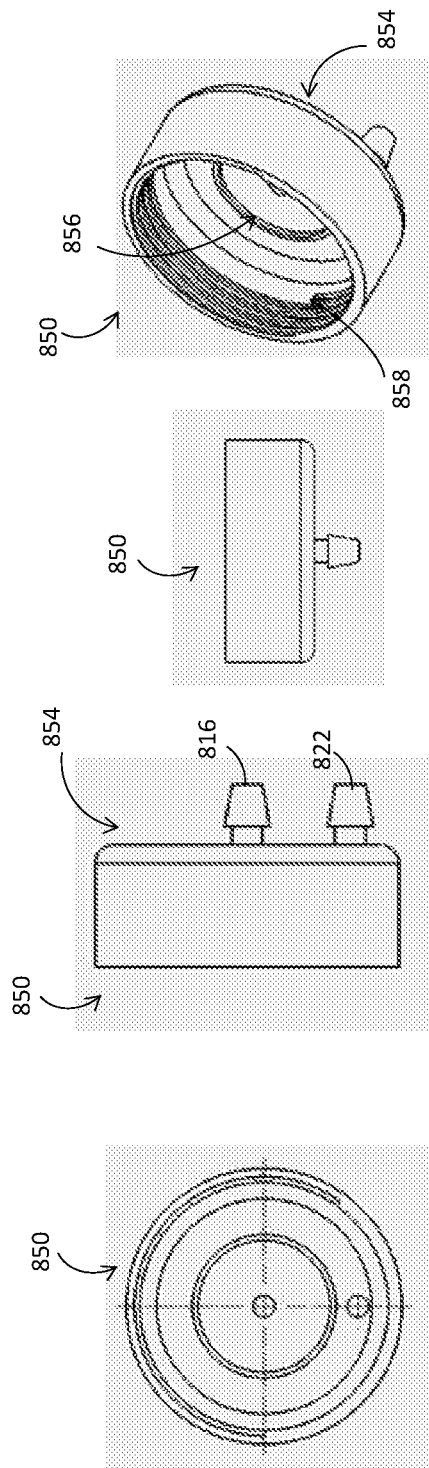

SYSTEMS, DEVICES, AND METHODS FOR EXTRACORPOREAL REMOVAL OF CARBON DIOXIDE

CROSS-REFERENCE TO RELATED APPLICATIONS

This application is a U.S. National Stage of International Patent Application No. PCT/US2018/051370, filed on Sep. 17, 2018, which claims priority to and the benefit of United States Provisional Patent Application No. 62/559,583, filed Sep. 17, 2017, the entire content of each of which is incorporated herein by reference.

FIELD

The present disclosure relates to systems, devices, and methods for low-flow extracorporeal removal of carbon dioxide to treat, for example, hypercarbic respiratory failure.

BACKGROUND

Hypercarbic respiratory failure (HRF) is a serious condition that occurs when subject's lungs are not able to remove carbon dioxide ($CO_2$) from the subject's body using normal respiration. As a result, inadequate alveolar ventilation causes excessive levels of carbon dioxide to be accumulated in the blood. HRF is a manifestation of a multiple of diseases of ventilation including but not limited to: chronic obstructive pulmonary disease (COPD)—commonly referred to as emphysema and/or chronic bronchitis, asthma, cystic fibrosis, obesity hypoventilation syndrome, pulmonary fibrosis, chronic lung allograft dysfunction, bronchiolitis obliterans syndrome, neuromuscular disorders such as amyotrophic lateral sclerosis and muscular dystrophy, myasthenia gravis, inflammatory neuromuscular disorders such as polymyositis, stroke, hypothyroidism, neurological disorders of ventilatory control, chest wall deformities such as pectus excavatum, and electrolyte abnormalities such as, for example, hypophosphatemia and hypomagnesemia. The increased amount of $CO_2$ present in the human body, clinically measured as an increased concentration of $CO_2$ in the blood, has etiology that is associated with impairments in respiratory drive (e.g., stroke or obesity hypoventilation), decreased neuromuscular function (e.g., muscular dystrophy or amyotrophic lateral sclerosis), and primary lung disease such as, e.g., COPD or interstitial lung disease.

Treatment of HRF includes using supplemental oxygen and non-invasive ventilatory support. Current standards require critically ill patients and patients that are not responding to non-invasive therapy to be treated via intubation and full mechanical ventilation. Mechanical ventilator support for treatment of HRF is a costly procedure, which requires intensive care unit (ICU) admission, and can in fact exacerbate patient's condition.

Accordingly, extracorporeal carbon dioxide removal ($ECCO_2R$) techniques have been developed, which do not require intubation and external ventilator support. $ECCO_2R$ systems, using gas exchange devices referred to as oxygenators, have been used in extraordinary cases at specialized hospitals for treatment of profound hypoxic respiratory failure for both delivering oxygen to and removing carbon dioxide from venous blood. Due to the small fraction of $CO_2$ dissolved in blood in the gaseous form (about 5%), to achieve clinically significant $CO_2$ removal, $ECCO_2R$ approaches typically necessitate drawing blood from a patient at a large flow rate to increase the amount of gaseous $CO_2$ being exposed to the $ECCO_2R$ device. Use of high flow rates requires use of withdrawal cannulae having a large bore size. Also, safe and proper placement of large-bore cannulae in a patient requires specialized clinical expertise. Highly trained, specialized medical professionals and support staff to manage such devices, however, may not be available in hospitals that would benefit from $ECCO_2R$ systems. For this and other reasons, clinical use of $ECCO_2R$ systems remains limited.

Accordingly, there remains a need for improved $ECCO_2R$ systems and methods which are less invasive than existing approaches and do not depend on specialized clinical expertise.

SUMMARY

Accordingly, in some aspects, the present invention provides devices, systems, and methods for extracorporeal $CO_2$ removal using a less invasive and more effective approach which does not depend on a highly specialized clinical expertise for patient treatment. Traditional $ECCO_2R$ technology only removes gaseous $CO_2$. However, the body's total $CO_2$ reserve remains high in the form of bicarbonate ion which is rapidly interconverted to $CO_2$ via the endogenous enzyme carbonic anhydrase. This sequestration of $CO_2$ necessitates long term use of a more invasive device until the levels of both gaseous $CO_2$ and bicarbonate are reduced to physiologic levels.

In some embodiments, a device, system, and method are provided that can remove both excessive dissolved $CO_2$ and excessive bicarbonate from blood of a patient diagnosed with a HRF or any other condition manifesting in inability to remove $CO_2$ buildup in the patient's blood. The dissolved $CO_2$ and bicarbonate can be removed from the patient's body and provide sufficient $CO_2$ clearance to be operated independently of other support modalities and return the patient to physiologic baseline, in the full range of blood dissolved $CO_2$ concentrations, with a lower bound of physiologic baseline, from about 20 mmol/L to an upper bound of 120 mmol/L or greater. By removing both bicarbonate and dissolved gaseous $CO_2$ at least partially simultaneously, a removal of a larger amount of effective $CO_2$, which is not dependent on gaseous $CO_2$ concentration, is achieved. By shifting focus to a larger scope and whole-body pH balance and $CO_2$ removal, capture of both bicarbonate ion and dissolved $CO_2$ allows both lower flow rates and reduced length of therapy.

The blood can be withdrawn from the patient at a low-flow rate such as, for example, a rate of smaller than 400 ml/min. Thus, a catheter, or another access tool, of a smaller size can be utilized to withdraw blood, as compared to existing approaches requiring larger vascular access tools. In this way, the devices and systems can be operated in any medical facility having nursing or traditional clinic staff, since participation of a highly specialized physician is not required. In some embodiments, the same type of vascular access tools that is used for renal dialysis can be employed, and the described techniques can therefore be used for administering treatment in community hospitals and clinics with dialysis infrastructure. Another advantage of the described techniques is that they allow for more efficient carbon dioxide removal while maintaining blood pH at a desired level and maintaining overall systemic homeostasis. Different membrane components can be utilized for removal of both dissolved $CO_2$ and bicarbonate from patient's blood, which can be done at least partially simultaneously or in any suitable order.

In the described embodiments, a system is provided having a device, or a cartridge, encompassing first and second membrane components. The first membrane component can have a sweep gas passing therethrough, and the second membrane component can have a dialysate composition, or dialysate, passing therethrough. A target fluid, such as, e.g., blood or another fluid, can be passed through the device on one side of the first and second membrane components, and the sweep gas and dialysate can be passed through the device on another side of the first and second membrane components, respectively.

In the described embodiments, a dialysate facilitates removal of bicarbonate from a target fluid. The dialysate can be a liquid composition having zero or a small amount of bicarbonate. The composition of the dialysate can be selected such that electrical charge neutrality is maintained. The second membrane component, which can be semipermeable to bicarbonate, can have the dialysate passing therethrough to remove the bicarbonate from the target fluid separated from the dialysate by the second membrane component. Electrolyte content of the target fluid can be measured during treatment using the described system, and a flow rate and/or content of the dialysate can be adjusted accordingly, to maintain electrical charge neutrality.

In some aspects, an extracorporeal system for removing carbon dioxide from a fluid is provided. The system can include a cartridge body, a first membrane component, a second membrane component, a first inlet in fluid communication with the first membrane, a first outlet in fluid communication with the first membrane component, a second inlet in fluid communication with the second membrane component, and a second outlet in fluid communication with the second membrane component. The cartridge body has a cavity, a longitudinal axis extending between first and second ends of the body, a fluid inlet adjacent to the first end, and a fluid outlet adjacent to the second end. The first membrane component disposed within the cavity is configured to remove gaseous carbon dioxide from the fluid passing from the fluid inlet in a first direction towards the fluid outlet. The second membrane component disposed within the cavity is configured to remove bicarbonate from the fluid passing between the fluid inlet and the fluid outlet. The first inlet in fluid communication with the first membrane component is configured to deliver a sweep gas to the first membrane such that the sweep gas is passed through the first membrane in a second direction, and the first outlet in fluid communication with the first membrane component is configured to receive the sweep gas passed through the first membrane. The second inlet in fluid communication with the second membrane component is configured to deliver a dialysate to the second membrane such that the dialysate is passed through the second membrane in a third direction, and the second outlet in fluid communication with the second membrane component is configured to receive the dialysate passed through the second membrane.

In some aspects, a method for removing gaseous carbon dioxide and bicarbonate from fluids is provided. The method can include removing a fluid from a patient via a cannula in fluid communication with the patient's body, and causing the fluid to enter an extracorporeal housing comprising a first membrane component and a second membrane component such that the fluid is placed in contact with exterior surfaces of at least one of the first and second membrane components. The method can further include passing a sweep gas through the first membrane component to cause gaseous carbon dioxide to transfer from the fluid into the sweep gas, passing a dialysate through the second membrane component to cause bicarbonate to transfer from the fluid into the dialysate, and causing the fluid to exit the housing after the fluid has passes through the housing such that the gaseous carbon dioxide and bicarbonate are removed from the fluid.

In some aspects, a method for treating a hypercarbic respiratory failure (HRF) is provided. In some embodiments, the method includes selecting a patient in need of HRF treatment, drawing blood from the patient at a rate smaller than 400 ml/min, and subjecting the blood to at least one membrane configured to remove gaseous $CO_2$ and bicarbonate from the blood to bring a carbon dioxide level in the blood to a baseline level.

In some aspects, a method for treating a hypercarbic respiratory failure (HRF) is provided. In some embodiments, the method includes selecting a patient in need of HRF treatment, drawing blood from the patient at a rate smaller than 400 ml/min, subjecting the blood to a first membrane component configured to remove gaseous $CO_2$ from the blood, the first membrane component having a sweep gas passing therethrough, and subjecting the blood to a second membrane component configured to remove bicarbonate from the blood, the second membrane component having a bicarbonate removal liquid passing therethrough. The bicarbonate removal liquid can have zero bicarbonate, and sodium and chloride in concentrations that allow maintaining electrical charge neutrality at the second membrane component. In some embodiments, the sweep gas has zero gaseous $CO_2$.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

BRIEF DESCRIPTION OF THE FIGURES

FIG. 7A is a perspective exploded view of a cartridge housing in accordance with some embodiments.

FIG. 7B is a side cross-sectional view of the cartridge housing of FIG. 7A.

FIG. 8A is a cross-sectional view of an end cap of a cartridge housing illustrating an inner surface of the end cap.

FIG. 8B is a side, cross-sectional view of the end cap of FIG. 8A.

FIG. 8C is another side, cross-sectional view of the end cap of FIG. 8A.

FIG. 8D is a perspective view of the end cap of FIG. 8A.

DETAILED DESCRIPTION

Figure 1:
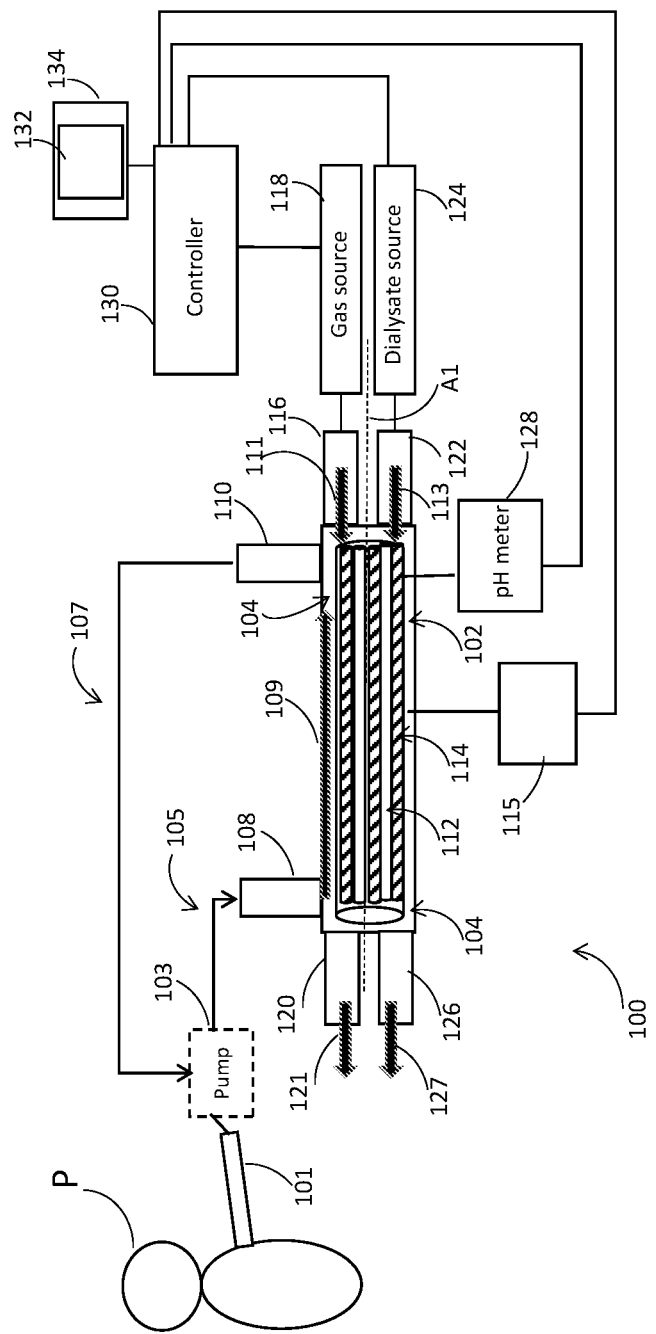
FIG. 1 is a diagram illustrating a system for carbon dioxide removal from patient's blood, in accordance with some embodiments.

The devices, systems, and methods described herein provide techniques for a safe and efficient removal of carbon dioxide from patient's blood or another fluid in an extracorporeal manner of a reduced complexity.

Although several extracorporeal carbon dioxide removal ($ECCO_2R$) approaches exist, they typically rely on high-rate blood flows because they are based on removing gaseous $CO_2$. Consequently, they are complicated to deploy and may lead to worsening of a patient's condition.

In blood, $CO_2$ exists in the forms of (1) dissolved gas (about 5%), (2) bound to hemoglobin (~5%), and (3) as a component of the bicarbonate ($HCO_3^-$) ion (about 90%) produced via the hydration of $CO_2$ in a reaction catalyzed by the carbonic anhydrase enzyme in human red blood cells. Due to the small fraction of total $CO_2$ present as dissolved gas in the blood, a traditional $ECCO_2R$ approach necessitates the use of a blood withdrawal cannula having a large bore size, so that adequate blood flow is generated to achieve clinically significant $CO_2$ removal that can lower total $CO_2$ content at a rate faster than accumulation and in a timescale that would be therapeutically feasible. The safe and proper placement of such cannulae requires specialized clinical expertise. Highly trained, specialized medical professionals, however, may not be always available in hospitals with $ECCO_2R$ systems. For this and other reasons, clinical use of $ECCO_2R$ systems remains limited.

Accordingly, to overcome the above disadvantages, the techniques described herein provide sufficient removal of carbon dioxide by removing both gaseous $CO_2$ dissolved in the blood, as well as bicarbonate that is the largest (about 90%) physiological store of effective $CO_2$ in venous blood. This hybrid approach allows the patient's blood to be drawn at flow rates of smaller than 400 ml/min, and catheters having a smaller diameter (which are less invasive and are easier to position) can thus be utilized. The gaseous $CO_2$ and bicarbonate are removed from the patient's blood while maintaining homeostasis and preventing undesirable local variation in blood pH levels. In some embodiments, local pH control at the $ECCO_2R$ device and reducing $CO_2$ load of the entire body back to physiologic levels drives restoration of homeostatic pH levels.

The described techniques can be used to treat patients having various degrees of respiratory failure and are not limited to application to patients that depend on mechanical ventilation support. In some embodiments, the described techniques can be used to remove carbon dioxide from a fluid, such as, e.g., blood, that contains from about 20 mmol/L to about 120 mmol/L of carbon dioxide (e.g., about 20 mmol/L, or about 30 mmol/L, or about 40 mmol/L, or about 50 mmol/L, or about 60 mmol/L, or about 70 mmol/L, or about 80 mmol/L, or about 90 mmol/L, or about 100 mmol/L, or about 110 mmol/L, or about 120 mmol/L) of carbon dioxide, and to return the content of $CO_2$ in the patient's blood to a baseline level of from about 23 mmol/L to about 29 mmol/L (e.g., about 23 mmol/L, or about 24 mmol/L, or about 25 mmol/L, or about 26 mmol/L, or about 27 mmol/L, or about 28 mmol/L, or 29 mmol/L). The techniques according to some embodiments allow to effectively bring the carbon dioxide content in the patient's blood to baselines levels while withdrawing the blood at a flow rate of smaller than 400 ml/min (e.g., less than about 400 ml/min, or less than about 350 ml/min, or less than about 300 ml/min, or less than about 250 ml/min, or less than about 200 ml/min, or less than about 150 ml/min, or less than about 100 ml/min, or less than 90 ml/min, or less than 80 ml/min, or less than 70 ml/min, or less than 60 ml/min, or less than 50 ml/min, or less than 40 ml/min, or less than 30 ml/min, or less than about 25 ml/min) while some existing approaches depend on a vascular-access flow rate of greater than 500 ml/min and typically greater than 1 L/min. As a result, the devices, systems, and methods according to some embodiments employ a catheter or access cannula used to withdraw blood from the patient's body that has a size of from about 8 Fr to about 13 Fr (e.g., from about 8 Fr to about 12 Fr, from about 8 Fr to about 11 Fr, or from about 8 Fr to about 10 Fr, or from about 8 Fr to about 9 Fr, or from about 9 Fr to about 13 Fr, or from about 9 Fr to about 12 Fr, or from about 9 Fr to about 11 Fr, or from about 9 Fr to about 10 Fr, or from about 10 Fr to about 12 Fr, or from about 11 Fr to about 12 Fr, or from about 12 Fr to about 13 Fr, or about 8 Fr, or about 9 Fr, or about 10 Fr, or about 11 Fr, or about 12 Fr, or about 13 Fr). The catheters of a reduced size that are used to acquire blood at low flow rates can be positioned at a patient's body in a less traumatic manner, such that a likelihood of clinical error is reduced or eliminated.

In the described embodiments, bicarbonate, along with gaseous carbon dioxide, is a target capture species. In some aspects, a dialysate for removing bicarbonate from blood has a composition that facilitates removal of bicarbonate from blood, which can be done at least partially simultaneously or substantially simultaneously with removal of gaseous carbon dioxide from the blood. In some embodiments, the dialysate for removing bicarbonate from blood includes zero bicarbonate. In other aspects, bicarbonate can be present in the dialysate in a concentration of less than about 38 mmol/L (e.g., less than about 35 mmol/L, or less than about 30 mmol/L, or less than about 25 mmol/L, or less than about 20 mmol/L, or less than about 15 mmol/L, or less than about 10 mmol/L, or less than about 5 mmol/L, or less than about 4 mmol/L, or less than about 3 mmol/L, or less than about 2 mmol/L, or less than about 1 mmol/L).

In the described techniques, the dialysate for removing bicarbonate from blood can include sodium and/or chloride in concentrations that facilitate removal of bicarbonate in a manner that maintains charge neutrality, as described in more detail below. Transfer of the negatively charged bicarbonate ions from blood into a dialysate can remain electrically neutral by transfer of positively charged ions into the dialysate from the blood, or transfer of negatively charged ions into the blood from the dialysate. Thus, either co-transport or counter-transport of ions, which have different transportation kinetics and membrane transport implications, can be utilized in embodiments in accordance with the described techniques, as also described in more detail below.

Because both bicarbonate and dissolved $CO_2$ are removed from blood or another fluid (e.g., blood plasma) in the described embodiments at least partially simultaneously or in a suitable order, no undesirable bulk shifts in chemical equilibrium occur that would alter pH beyond normal physiological levels. In some embodiments, local alkalinity of blood may be therapeutically desirable to drive the patient's overall state from acidosis. This local alkalinity may be outside of normal physiologic levels but controlled.

An extracorporeal system, or circuit, in accordance with the described techniques can have various configurations. FIG. 1 illustrates an example of an extracorporeal system 100, which can also be referred to as an extracorporeal circuit, for removing carbon dioxide from a fluid in the form of both gaseous $CO_2$ and bicarbonate, in which some embodiments described herein can be implemented. As shown, the system 100 includes a cartridge, or cartridge housing, 102, that can be an elongate member having a chamber or cavity 104 therein. In some embodiments, the cartridge 102 can be a generally tubular member, though it can have other shapes. The cartridge housing 102 has a longitudinal axis A1 extending between a first end 106a and second end 106b of the housing 102, a fluid inlet 108 adjacent to the first end 106a, and a fluid outlet 110 adjacent to the second end 106b. A fluid such as, for example, blood, can be withdrawn from a patient via a catheter 101, delivered into the cavity 104 through the fluid inlet 108, and passed from the fluid inlet 108 through the cavity 106 towards the fluid outlet 110. The blood can be treated using a suitable anti-coagulation technique, which can be a technique similar or identical to pre-conditioning blood for dialysis or other procedures. The catheter 101 can be any suitable access tool configured to access the patient's vascular system.

In the illustrated embodiments, the catheter 101 has an outer diameter having a size of from about 8 Fr to about 13 Fr (e.g., from about 8 Fr to about 12 Fr, from about 8 Fr to about 11 Fr, or from about 8 Fr to about 10 Fr, or from about 8 Fr to about 9 Fr, or from about 9 Fr to about 13 Fr, or from about 9 Fr to about 12 Fr, or from about 9 Fr to about 11 Fr, or from about 9 Fr to about 10 Fr, or from about 10 Fr to about 12 Fr, or from about 11 Fr to about 12 Fr, or from about 12 Fr to about 13 Fr, or about 8 Fr, or about 9 Fr, or about 10 Fr, or about 11 Fr, or about 12 Fr, or about 13 Fr). The catheter having a reduced size compared to catheters or cannulae for other extracorporeal devices can be deployed by a clinician without highly specialized training. Moreover, placement of such a reduced-size catheter is less traumatic to the patient and therefore reduces a likelihood of complications.

FIG. 1 illustrates schematically that the blood is passed from the fluid inlet 108 towards the fluid outlet 110 the along the longitudinal axis A1 in a first direction 109. The blood can be withdrawn from the patient's body via an input line 105 at a flow rate less than about 400 ml/min. For example, the blood can be withdrawn from the patient's body at an average rate of about 100 mL/min, about 125 mL/min, about 150 mL/min, about 175 mL/min, about 200 mL/min, about 225 mL/min, about 250 mL/min, about 275 mL/min, about 300 mL/min, about 325 mL/min, about 350 mL/min, about 375 mL/min, about 400 mL/min, or any flow rate between of the above values, such that there is a bulk movement of blood forward through the circuit. After the blood has passed through the cartridge 102, a return line 107 delivers the treated blood back into the patient's vascular system. The input line 105 and return line 107 can have tubing, access ports, and other suitable component(s) that are not shown in detail in FIG. 1.

As shown in FIG. 1, the system 100 can include a pump 103 configured to operate to pump the blood from a patient P and to cause the blood to pass through the cartridge housing 102. However, it should be appreciated that, in some embodiments, the system 100 may not include a pump, and the blood is caused to pass through the cartridge via other ways.

In the described embodiments, excessive carbon dioxide ($CO_2$), in the form of dissolved gaseous $CO_2$ and bicarbonate, is removed from the patient's blood as the blood is passed through the cartridge housing 102. For example, in some embodiments, the cartridge includes components providing liquid-liquid and liquid-gas exchange interfaces with a liquid (e.g., a dialysate liquid) and a gas, respectively. The patient's blood is brought in contact with such exchange interfaces, and the dialysate liquid and gas act as sweep components for the respective exchange interfaces.

Accordingly, as FIG. 1 illustrates, the inner cavity 104 includes a first membrane component 112 configured to remove gaseous $CO_2$ from the fluid passing from the fluid inlet 108 towards the fluid outlet 110, and a second membrane component 114 configured to remove bicarbonate from the fluid passing from the fluid inlet 108 towards the fluid outlet 110. In some embodiments, the first membrane component 112 and the second membrane component 114 can each be in the form of a plurality of hollow fibers that can have one or more different properties among the first and second membrane components 112, 114. In some embodiments, the second membrane component 114 can be an ultrafiltration membrane. It should be noted that first and second membrane components 112, 114 can be in the form of one or more other elements having various properties.

As further shown in FIG. 1, the cartridge 102 includes a first inlet 116 in fluid communication with the first membrane component 112 and configured to deliver a sweep gas to the first membrane component 112 from a gas source 118. The sweep gas source 118 can deliver the gas or a mixture of gases such as, for example, a pressurized air or another gas that can be equivalent to room air. In the illustrated embodiments, the sweep gas can have a zero to low concentration of $CO_2$. For example, the sweep gas can have a low content of $CO_2$—e.g, from about 0 parts per million (ppm) to about 66,000 ppm. In some embodiments, the sweep gas including zero to low $CO_2$ can be a gas having 100% oxygen, or 100% nitrogen, or 100% argon, or any combination of nitrogen, oxygen, and/or argon. In some embodiments, the sweep gas can be room air including 78% nitrogen, 21% oxygen, and 1% trace gases. However, the sweep gas can have any other suitable content. In the described embodiments, the sweep gas is biocompatible and inert and gases such as, for example, carbon monoxide, are not used in the sweep gas. The system 100 operates such that the sweep gas is passed through the first membrane component 112 in a second direction (schematically shown by an arrow 111 in FIG. 1) such that the sweep gas exits (arrow 121) the cartridge 102 via a first outlet 120 that is in fluid communication with the first membrane component 112. It should be appreciated that, depending on the configuration and position of the first membrane component 112 within the cartridge 102, the direction of the sweep gas as it passes through the cartridge 102 can change.

The cartridge 102 also includes a second inlet 122 in fluid communication with the second membrane component 114 and configured to deliver a dialysate fluid to the second membrane component 114 from a dialysate source 124. In the illustrated embodiments, the dialysate has a concentration of bicarbonate less than the concentration of bicarbonate in the blood before the blood is treated. Thus, in some embodiments, the dialysate has zero bicarbonate. Additionally, or alternatively, the dialysate can have a level of sodium (e.g., from about 0 mmol to about 200 mmol) that promotes co-transport of ion species across the second membrane component 114 to maintain electrical neutrality.

Bicarbonate is a charged ion and any diffusion of bicarbonate against a concentration gradient across a membrane (e.g., a semi-permeable membrane) will act to create an electrical field that counteracts further net diffusion of bicarbonate. Accordingly, in the described embodiments, net charge neutrality between two compartments or areas separated by the semi-permeable membrane is maintained to allow diffusion of bicarbonate across a semi-permeable membrane for adequate bicarbonate removal of a treated fluid (e.g., blood). In some embodiments, coupling bicarbonate transport with transport of another ion, either a positive ion moving in the same direction or a negative ion moving in the opposite direction, can provide for maintenance of charge balance or charge neutrality.

In some embodiments, the dialysate can have a level of sodium that promotes transport of sodium from the blood to the dialysate to couple with bicarbonate transport to maintain charge neutrality. Other positive ions present in the body include calcium, magnesium, and potassium, but, among the positive ions present in the body, sodium is the one present in the adequate concentration to be used for the purposes of maintaining charge neutrality in accordance with the described techniques. In addition, loss of sodium during treatment can be compensated by an infusion of NaOH (or other sodium salt(s)) post-treatment.

In some embodiments, the dialysate can have a level of chloride that promotes transport of chloride from the dialysate into the blood to couple with the bicarbonate transport to maintain charge neutrality.

In the described embodiments, a dialysate composition can be selected such that a dialysate promotes either transport of sodium from the blood to the dialysate along with transport of bicarbonate from the blood into the dialysate, or a dialysate promotes transport of chloride from the dialysate into the blood along with transport of bicarbonate from the blood into the dialysate. Regardless of whether a co-transport (e.g., Na—$HCO_3$ co-transport) or counter-transport (e.g., Cl—$HCO_3$ counter-transport) approach is utilized, the dialysate composition is selected so as to maintain charge neutrality.

In some embodiments, the dialysate composition that facilitates bicarbonate diffusion across a membrane component is selected based on properties of the patient's blood (or another target fluid that can be treated using the described techniques). For example, the dialysate composition can be selected based on the content of sodium and/or chloride in the patient's blood. Thus, in some embodiments, if the patient is determined to have a higher starting Na level (e.g., greater than about 140 mEq/L, or greater than about 150 mEq/L, or greater than about 155 mEq/L), the Na—$HCO_3$ co-transport approach can be utilized to remove bicarbonate from the patient's blood. Alternatively, if the patient is determined to have a lower starting Na level (e.g., less than about 140 mEq/L, or less than about 135 mEq/L, or less than about 130 mEq/L, or less than about 125 mEq/L, or less than about 120 mEq/L), the Cl—$HCO_3$ counter-transport can be utilized to remove bicarbonate from the patient's blood. The selection between the co-transport and counter-transport approaches (and respective dialysate composition) can additionally or alternatively be done based on other factors, such as, e.g., one or more patient's characteristics, patient's medical condition, patient's prior medical history and treatments, etc.).

In some embodiments, sodium and chloride concentration of the dialysate can be selected based on patient's blood content, and either co-transport or counter-transport of ions across a membrane in contact with the dialysate (e.g., a dialysate semi-permeable to bicarbonate) can be utilized depending on the patient's blood content. For example, a co-transport mechanism can be utilized when the patient's blood has an increased sodium concentration, in which case the dialysate sodium concentration is selected to be lower than the sodium concentration in the patient's blood, while chloride concentration in the dialysate can be approximately the same as chloride concentration in the patient's blood. For example, if patient's venous blood has sodium concentration of about 150 mEq/L (the normal physiological concentration of sodium is about 140 mEq/L) and chloride concentration of about 110 mEq/L, to promote sodium and bicarbonate co-transport from the blood to the dialysate, the dialysate can be prepared such that it has sodium concentration of about 110 mEq/L, chloride concentration of about 110 mEq/L, and zero bicarbonate. In this way, the sodium and bicarbonate will move from the blood to the dialysate.

In embodiments in which the dialysate's composition is selected to promote co-transport of sodium and bicarbonate from the patient's blood to the dialysate, the dialysate can have a concentration of sodium from about 90 mEq/L to about 180 mEq/L (e.g., about 90 mEq/L, or about 100 mEq/L, or about 110 mEq/L, or about 120 mEq/L, or about 130 mEq/L, or about 140 mEq/L, or about 150 mEq/L, or about 160 mEq/L, or about 170 mEq/L, or about 180 mEq/L). The upper bound of the sodium concentration in the dialysate can be determined based on the concentration of sodium in the patient's blood, as discussed above.

In some embodiments, the dialysate has zero bicarbonate and its composition is selected to promote counter-transport of chloride from the dialysate to the blood and bicarbonate from the blood to the dialysate. In some embodiments, to utilize counter-transport, chloride concentration in the dialysate is selected to be higher than chloride concentration in the patient's blood, while sodium concentration in the dialysate is selected to be approximately the same as sodium concentration in the patient's blood. The counter-transport mechanism can be utilized when the patient's blood has a decreased sodium concentration. For example, if patient's venous blood has sodium concentration of about 130 mEq/L (the normal physiological concentration of sodium is about 140 mEq/L) and chloride concentration of about 110 mEq/L, to promote chloride and bicarbonate counter-transport from the blood to the dialysate, the dialysate can be prepared such that it has sodium concentration of about 130 mEq/L, chloride concentration of about 140 mEq/L, and zero bicarbonate. The lower bound of chloride concentration can be determined by the sodium concentration of the patient's blood. The dialysate can have a chloride concentration from about 80 mEq/L to about 170 mEq/L (e.g., about 80 mEq/L, or about 90 mEq/L, or about 100 mEq/L, or about 110 mEq/L, or about 120 mEq/L, or about 130 mEq/L, or about 140 mEq/L, or about 150 mEq/L, or about 160 mEq/L, or about 170 mEq/L) with a lower bound determined by the sodium concentration of the patient.

Sodium and chloride are dominant ions in the human body, and, in the described embodiments, they can be selected for inclusion in the dialysate in order to not induce excessive changes in the blood content, such that the dialysate is safe for the patient. It should be noted that the blood can be treated using the described techniques for a certain duration of time, selected so as not to cause undesirably low sodium and/or chloride levels of the returned blood.

In some embodiments, other ions can be selected in addition to or instead of sodium and/or chloride, and electroneutrality in the dialysate/blood interface will be maintained. In such embodiments, the blood will need to be replenished with chloride and sodium.

In some embodiments, regardless of whether a co- or counter-transport approach is employed, the composition of the dialysate can be adjusted during treatment, to counteract any undesirable variations in electrolyte gradient. In this way, charge neutrality can be maintained. For example, electrolyte content of the patient's blood passing through a device including membrane(s) (e.g., cartridge 102 of FIG. 1) can be analyzed, and it can be determined, based on results of the analysis, whether to adjust the composition of the dialysate. The electrolyte content of the patient's blood can be determined via a suitable lab test (e.g., a basic metabolic panel) or using another one or more approaches.

Furthermore, in some embodiments, the device can include one or more electrolyte sensors configured to measure electrolyte content of the blood as the blood is being passed through the cartridge. FIG. 1 shows that the system 100 can include an electrolyte sensor 115 configured to measure electrolyte content of the blood in the cartridge, and the acquired measurements can be used to determine whether sodium and/or chloride levels in the blood have changed beyond a threshold and whether the levels need to be adjusted. It should be appreciated that the electrolyte sensor 115 is shown in FIG. 1 by way of example, as the system 100 can include more than one electrolyte sensors positioned at a suitable location to measure electrolyte content of fluids disposed within the cartridge 102.

It should be appreciated that a dialysate formulated for removal of bicarbonate from blood or another fluid can have other suitable compositions. For example, in some aspects, non-limiting examples of dialysate include a plasma solution, a water solution, or any other liquid or non-liquid fluid that can be passed through the device to facilitate blood or other fluid treatment via ion transport. Further, in embodiments in which membranes are not anion-specific and only size-specific, anions can be used.

Referring back to FIG. 1, the system 100 can operate such that the dialysate is passed through the second membrane component 114 in a third direction (schematically shown by an arrow 113 in FIG. 1) and exits (arrow 127) the cartridge 102 via a second outlet 126 in fluid communication with the second membrane component 114. The spent dialysate can be collected (e.g., in a waste reservoir) and discarded. It should be appreciated that, depending on the configuration and position of the second membrane component 114 within the cartridge 102, the direction of the dialysate as it passes through the cartridge 102 can change.

In the illustrated example of FIG. 1, as schematically shown in FIG. 1, the third direction 113 is substantially parallel to the second direction 111, and the second and third directions 111, 113 are substantially opposite to the first direction 109. However, in some embodiments, the second and third directions 111, 113 can be different from one another (e.g., at an angle with respect to one another), and they have can a different relationship relative to the first direction 109. The directions at which the sweep gas and dialysate are passed through cartridge 102 can depend on the configuration and position of the membrane components. For example, in embodiments in which the first and second membrane components, or at least portions thereof, are angled with respect to one another, the second and third directions 111, 113 can be accordingly along axes that are angled with respect to one another.

The system 100 can include other components such as, for example, the electrolyte sensor 115 and a pH meter 128 that is configured to measure a pH of fluids (e.g., blood and/or dialysate) contained in the cartridge 102. It should be appreciated that the position of the pH meter 128 is shown in FIG. 1 by way of example only, as the pH meter 128 can be positioned in any suitable way within the system 100. Moreover, in some implementations, the system 100 can have more than one pH meters positioned so as to measure pH of fluids within the cartridge 102. For example, a pH meter can measure pH of the blood as it enters the cartridge, pH of the blood within the cartridge (after the blood has been at least partially treated), and pH of the blood as it exits the cartridge. In addition, it should be appreciated that pH of the blood can be measured outside the cartridge. The system 100 can include other suitable components (e.g., a heat exchanger) that are not shown in FIG. 1.

As further shown in FIG. 1, in the illustrated embodiment, the system 100 includes a controller 130 configured to control operation of the system's components. Thus, the controller 130 is configured to monitor system's conditions and to adjust operation of one or more of the system's components in response to the monitored system's conditions. For example, in some embodiments, the controller 130 can control adjustment of one or more of a blood flow rate, a flow rate of a dialysate delivered from the dialysate source 124, a flow rate of gas delivered from the gas source 118, a composition of the dialysate, and/or a composition of the gas. This can be done, for example, in response to electrolyte content of fluid(s) within the cartridge 102 (e.g., measured using the electrolyte sensor(s) 115) and/or in response to pH values of fluid(s) within the cartridge 102 (e.g., measured using the pH meter(s) 128). The controller 130 can be configured to control various parameters of the system 100 automatically, which can be done prior to or during the operation of the system. For example, in some embodiments, one or both a flow rate and content of the dialysate can be controlled by the controller 130 automatically, in response to measurements of the electrolyte content and other parameters (e.g., pH) of the blood passing through the cartridge 102.

In some implementations, various parameters of the system 100 can be controlled based on user input, which can be done using the controller 130 or via other device(s). For example, the controller 130 can have or can be associated with one or more input devices (e.g., control panel(s), buttons, knobs, user interfaces, etc.) configured to receive user input instructing the controller or other component(s) of the system 100 to adjust operating parameter(s) of the system 100. The control can be also performed such that some of the parameters are controlled automatically by the controller 130 whereas some of the parameters are controlled based on user input.

The controller 130 can additionally or alternatively control operation of the system 100 based on various other parameters that can be acquired during operation of the system 100. For example, a flow rate and/or composition of a reconditioning fluid can be controlled in some embodiments, as discussed in more detail below.

In some embodiments, the controller can be configured to alter the relative capture rates of bicarbonate and dissolved $CO_2$, which, per the Henderson-Hasselbalch equation, alters pH. The controller can additionally or alternatively control altering of delivery and/or composition of additional buffers to the system. The relative capture rates can be altered by changing the effective membrane surface area for each capture species, the sweep flow rates for both liquid and gas, or the amount of blood exposed to each membrane surface. The effective surface area can be altered by dynamically changing the available pathway of blood or sweep fluid through the device.

The controller 130 can have any suitable configuration. For example, it can be or it can be associated with a computing device having at least one processor and memory storing computer-executable instructions for execution by the at least one processor. The controller 130 can include or can be associated with a display 132 configured to provide a user interface 134 that can present information to a user of the system 100 (e.g., a clinician operating the system 100) during a treatment of the patient or at any other suitable time. For example, the user interface 134 can display, in any suitable visual, audio, etc. format, information to the user indicating a progress of the treatment. In some implementations, the display 132 can be a touch panel display configured to receive user input for controlling operation of the system 100, user input for controlling the way in which data is presented on the display 132, and/or any other type of user input.

Figure 2:
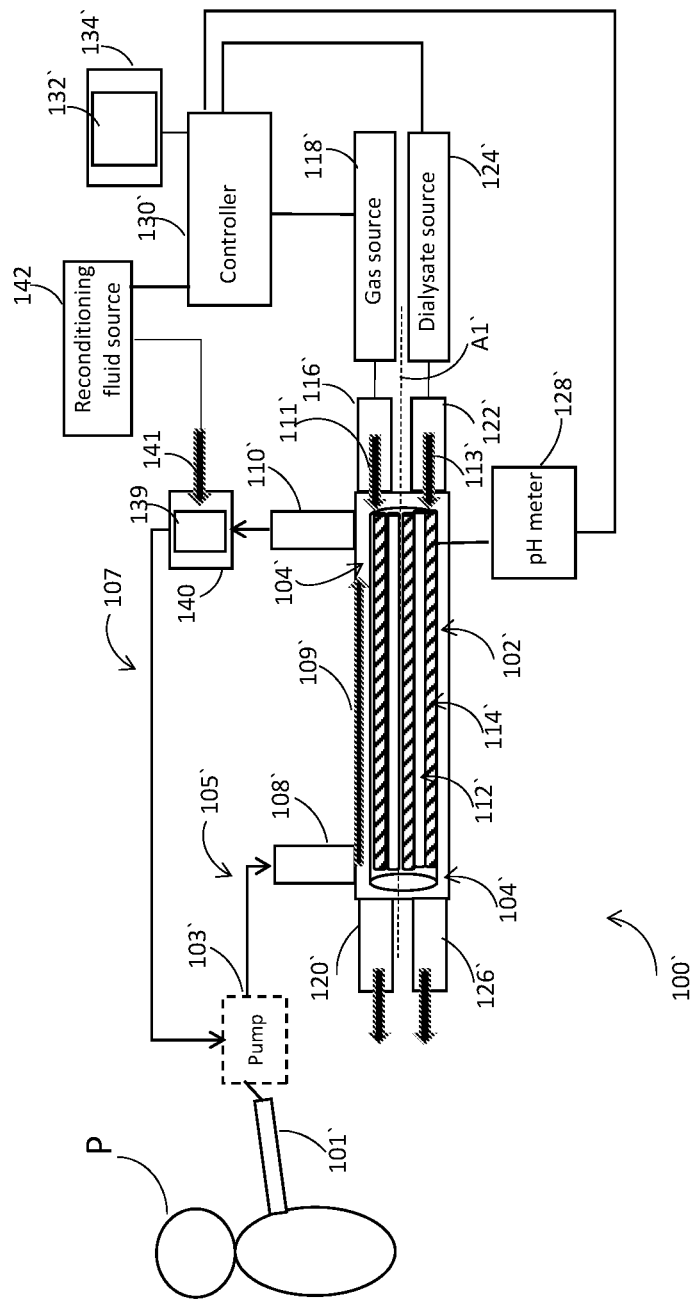
FIG. 2 is a diagram illustrating a system for carbon dioxide removal from patient's blood, the system including reconditioning fluid components.

In the illustrated embodiments, as mentioned above, homeostasis is maintained, which involves maintaining pH of the blood or another target fluid at a desired level. The system 100 can include one or more components configured to recondition the patient's blood. Thus, FIG. 2 illustrates a system 100' which includes components similar to components of FIG. 1, such as a cartridge 102', a fluid inlet 108', a fluid outlet 110', first and second inlets 118', 124', first and second outlets 120', 126', and other components which are similar to components of FIG. 1. Components of FIG. 2 that are similar to corresponding components of FIG. 1 are labeled with corresponding similar reference numerals with a prime superscript. Also, although not shown in FIG. 2, similar to system 100 of FIG. 1, the system 100' can include one or more electrolyte sensors.

As shown in FIG. 2, the system 100' includes a reconditioning component 140 (e.g., a chamber) that includes a membrane component 139, which can be referred to as a third membrane component. The membrane component 139 provides an interface between a target fluid (e.g., blood) and a reconditioning, or rebalancing, fluid supplied (arrow 141) to the reconditioning component 140 from a reconditioning fluid source 142. It should be appreciated that the direction and location at which the reconditioning fluid is delivered into the reconditioning component 140 are shown by arrow 141 in FIG. 2 by way of example only. The reconditioning fluid is passed through the reconditioning component 140 such that the blood content is adjusted prior to returning the blood to the patient's body. The adjustment can involve adding certain elements to the blood and/or removing certain elements from the blood. The reconditioning component 140 can be associated with other components (e.g., a pH meter, an electrolyte sensor, etc.) configured to measure or monitor one or more parameters of the blood being treated in the reconditioning component 140. A controller, such as, in the example of FIG. 2, a controller 130', can control a flow rate and/or content of the reconditioning fluid delivered into the reconditioning component 140 based on the one or more measured or monitored parameters. The controller 130' can be configured to control any other parameters that affect treatment of blood or another fluid by the reconditioning component 140.

In some embodiments, as shown in FIG. 2, the reconditioning component 140 is positioned outside of the cartridge 102' such that the membrane 139 operates as a post-exchange membrane for adjusting blood content after the blood has passed through the cartridge 102' and gaseous carbon dioxide and bicarbonate are removed from the blood. It should be appreciated, however, that the reconditioning component 140, which can have any suitable configuration, can be disposed in any other manner within the system 100'. For example, in some implementations, the reconditioning component 140 can be disposed within the cartridge 102'. In such embodiments, the blood can be reconditioned at least partially simultaneously with removal of excess of carbon dioxide from the blood. A controller (e.g., controller 130') can control the process of blood reconditioning, by controlling, e.g., a flow rate and/or content of the reconditioning fluid, to adjust the blood content in accordance with desired blood characteristics.

In some implementations, the cartridge 102' can have additional inlet and outlet ports through which a (re)conditioning fluid can enter and exit the cartridge cavity, respectively. A system controller such as, e.g., a controller 130' can be configured to control delivery of the reconditioning fluid to the blood. This can be performed in response to parameters of the system 100', which can be acquired as the operation of the system 100' is being monitored. For example, pH values of the blood and/or dialysate included in the cartridge 102' can be acquired and a flow rate of the reconditioning fluid can be adjusted in response to the pH value measurements. In some embodiments, additionally or alternatively, a composition and/or a content of the reconditioning fluid can be adjusted in real-time, during operation of the system 100' as the patient is being treated. For example, reconditioning fluids can be used to introduce or remove additional buffers to control blood pH. Non-limiting examples of a biocompatible buffer include monoethanolamine, hydrochloric acid (at low concentrations), or sodium hydroxide. Reconditioning fluids can also include sodium, potassium, chloride, glucose, or other blood constituents to the body. These ionic constituents can be included in the reconditioning fluid so that they are within +−100% of the normal physiologic level of these ions found in blood. For example, sodium, which normally exists at about 140 mmol/L in blood, can be present in a reconditioning fluid at a level from about 0 mmol/L to about 280 mmol/L.

A post-conditioning procedure involving treating blood may be selected based on blood condition. For example, if blood is characterized by hyponatremia, this can be corrected by bringing the blood in contact with a post-exchange membrane with a saline solution, to adjust sodium levels to normal values. The blood content can be adjusted by adding one or more constituents such as, e.g., glucose, magnesium, potassium, and calcium. In addition to off-target capture effects, additional pH balancing may be performed. Since the patient's total blood pool will typically be net acidotic in the setting of HRF, it is desirable to return to the patient blood with increased pH, to help neutralize as well as lower net $CO_2$ load. To do this, the reconditioning step can involve adding a reconditioning buffer such as, e.g., monoethanolamine (MEA), at various concentrations. Sodium hydroxide can also be used in the reconditioning buffer at various concentrations, which can result in simultaneously correcting for hyponatremia. The buffer composition can be selected based on whether there is a need for pH adjustment. For example, sodium hydroxide (as a stronger base) may be used when the degree of acidemia exceeds the basicity of MEA.

In some aspects, first and second membrane components included in a hybrid cartridge (e.g., the first and second membrane components 112, 114 or 112', 114') can have any suitable configuration. In some embodiments, the first and second membrane components are in the form of a plurality of hollow membrane fibers. In some embodiments, a sweep gas and a sweep liquid (dialysate) are delivered into the interior of the first and second membrane components in the form of hollow membrane fibers, respectively. The blood being transferred through the interior of the cartridge is brought in contact with the first and second hollow membrane fibers, such that the blood washes over the exterior surfaces of these components. The sweep gas passed through the interior of the first membrane component in the form of first hollow fibers causes dissolved $CO_2$ to be removed from the blood, and the dialysate passed through the interior of the second membrane component in the form of second hollow fibers causes bicarbonate to be removed from the blood.

The dissolved $CO_2$ and bicarbonate can be removed from blood using the described devices, systems, and methods substantially simultaneously or in any suitable order. In the embodiments illustrated in FIGS. 1 and 2, the hybrid cartridge includes both first and second membrane components and the dissolved $CO_2$ and bicarbonate can therefore be removed from blood substantially simultaneously, where "substantially" means that effective removal of dissolved $CO_2$ and effective removal of bicarbonate coincide in time. However, in some implementations, as discussed in more detail below, a system in accordance with the described techniques can be configured such that dissolved $CO_2$ is removed from the blood before bicarbonate is removed from the blood, or bicarbonate is removed from the blood before dissolved $CO_2$ is removed from the blood. These can occur in the same or separate extracorporeal circuits that are operated concurrently and/or sequentially.

The first and second membrane components, which can be different from one another, can be disposed within the hybrid cartridge in various ways and in various relationship with respect to each other. For example, in some embodiments, the first and second membrane components can be in the form of elongate fibers disposed within the cartridge such that the fibers (their long sides) are substantially parallel to a longitudinal axis to the cartridge. Such an implementation is shown schematically in FIGS. 1 and 2. The fibers forming the first and second membrane components can be disposed in a complex arrangement, which can be a random arrangement or an arrangement forming a certain pattern (including one or more regular patterns). In some embodiments, the fibers can be intermingled within the cartridge or they can be disposed within the cartridge in other ways.

Figure 3:
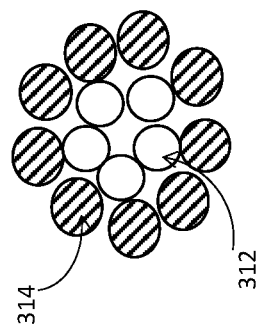
FIG. 3 is a cross-sectional view of an example of first and second membrane components disposed in a cartridge of a system for carbon dioxide removal from patient's blood, in accordance with embodiments.

FIG. 3 illustrates an example in which a first membrane component 312, in the form of hollow fibers configured to receive a sweep gas therethrough, are disposed in a circular manner, and a second membrane component 314, in the form of hollow fibers configured to receive a dialysate therethrough, are arranged in a circular manner around the first membrane component fibers 312. It should be noted that more than one row of the first membrane component fibers 312 and/or more than one row of the second membrane component fibers 314 can be formed. As another variation, the first and second membrane fibers can be disposed concentrically with respect to one another in other ways. The first membrane component fibers 312 and the second membrane component fibers 314 can have different lengths along a length of the cartridge. For example, the first membrane component fibers 312 can be shorter or longer than the second membrane component fibers 314.

Figure 4:
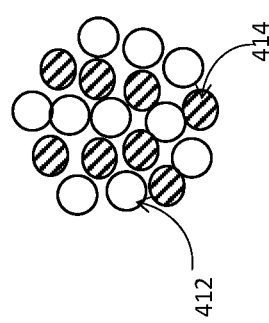
FIG. 4 is a cross-sectional view of another example of first and second membrane components disposed in a cartridge of a system for carbon dioxide removal from patient's blood, in accordance with embodiments.

FIG. 4 illustrates another example of an arrangement of first and second membrane components where the first and second membrane component fibers 412, 414 are intermingled in a random manner. The first and second membrane component fibers 412, 414 can have different lengths. Additionally, or alternatively, the fibers forming the first membrane component 412 can have different lengths (such that at least some of the fibers are longer than other fibers), and the fibers forming the second membrane component 414 can have different lengths. In some embodiments, each of the first membrane component fibers 412 has a different length (shorter or longer) than each of the second membrane component fibers 414.

Figure 5:
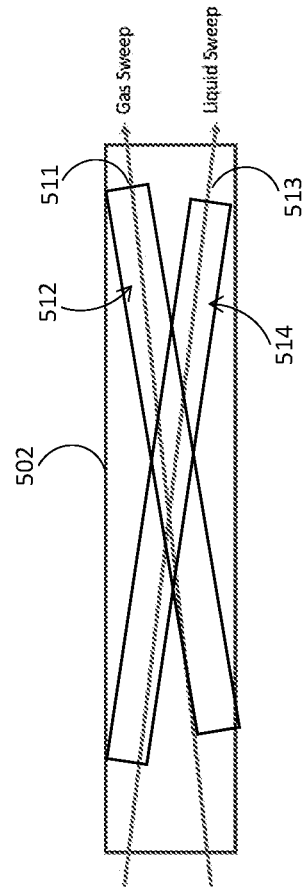
FIG. 5 is a side cross-sectional, partially transparent view illustrating schematically of first and second membrane components in a cartridge of a system for carbon dioxide removal from patient's blood, and illustrating a direction of a flow of a sweep gas through the cartridge and a direction of a flow of dialysate through the cartridge.

FIG. 5 shows another embodiment of an arrangement of first and second membrane components in which the first and second membrane components 512, 514 are arranged diagonally with respect to one another within a cartridge 502 along a length L of the cartridge 502. FIG. 5 also shows schematically a direction 511 along a first axis in which a sweep gas is passed through the first membrane component 512, and a direction 513, along a second axis that is angled with respect to the first axis, in which a dialysate is passed through the second membrane component 514. In some embodiments, the fibers forming the first and second membrane components 512, 514, respectively, can be bundled together such that the first membrane components 512 form a bundle and the second membrane components 514 form a bundle. In some embodiments, the first and second membrane components 512, 514 are disposed in the alternating manner within the cartridge 502, such that one or more elongate fibers of the first membrane component 512 alternate with one or more elongate fibers of the one or more elongate fibers of the second membrane 514. In other implementations, the fiber components 512 and 514 can be arranged so as to form any type(s) of concentric, adjacent, crossing, or separating geometries. In this example, the blood can be pumped through the cartridge such that it washes over the exterior surface of the fibers forming the first and second membrane components.

First and second membrane components, which can be formed from fibers of different types, can be included in a hybrid cartridge in accordance with the described techniques in any suitable ratio. The ratio can be selected based on a desired carbon dioxide capture rate and pH balance. For example, in some embodiments, the first membrane/second membrane ratio can be a 1:1 ratio. Non-limiting examples of other ratios include 10:1, 100:1, 1000:1, 1:10, 1:100, 1:1000, or any other ratio.

First and second membrane components can be formed from various materials. In some embodiments, the first membrane component is formed from first fibers and the second membrane component is formed from second fibers that are different from the first fibers in one or more properties. For example, in at least some embodiments, the first membrane components can be formed from polymethylpentene to provide efficient gas-liquid exchange, where the polymethylpentene material prevents the penetration of liquid into the sweep gas side of the membrane. Other polymer membranes including other materials such as, for example, silicone, can be used.

The first and second membrane components can be formed from semi-permeable materials and they can have pores of a suitable size. For example, the second membrane component can be formed from one or more materials that are semi-permeable to bicarbonate, such as, for example, silicone, polyethersulfone (PES), PES with polyvinylpyrrolidone (PVP) fibers (e.g., PUREMA fiber manufactured by 3M Deutschland GmbH).

A gas used in the described embodiments for transfer of a target fluid across a gas-liquid barrier can have various composition, and it can be air, or another gas or mixture of gasses, as discussed above.

In the described embodiments, as discussed above, a dialysate or dialysate fluid is designed for transfer of a target fluid across a liquid-liquid barrier such that the dialysate has a composition that facilitates co-transport to maintain electrical neutrality of the fluid. In other embodiments, the dialysate can comprise a liquid composition suitable for counter transport to maintain electrical neutrality of the target fluid. The molarity of dialysate constituents may depend on the patient's condition that can be assessed from blood tests. For example, in one embodiment, a patient with relatively normal sodium in the patient's blood will have a dialysate content of sodium that is larger than about 140 mmol/L. In some embodiments, the dialysate comprises at least one of sodium chloride, bicarbonate, potassium, calcium, phosphate, sulfate, magnesium and any combination of other ions. In the dialysate of the described techniques, all ions, except sodium and bicarbonate, are at physiologically normal levels or within a range of +−15% of normal reference levels.

A reconditioning, or rebalancing, fluid used in the described embodiments can have various compositions. In some embodiments, the reconditioning fluid can comprise at least one biocompatible organic base, which can be, in some examples, monoethanolamine (MEA). Additionally or alternatively, the reconditioning fluid comprises at least one of sodium chloride, bicarbonate, potassium, calcium, phosphate, sulfate, and magnesium.

As mentioned above, the systems 100 (FIG. 1) and 100' (FIG. 2) can have various components. In some implementations, the systems 100, 100', or any other system configured to implement the described techniques, can be configured similar to a renal dialysis system. In this way, a cartridge, such as the cartridge 102 (FIG. 1) or 102' (FIG. 2) can be configured to be coupled to a renal dialysis system such that the dialysis system becomes capable of controlling levels of carbon dioxide in a patient in accordance with the techniques described herein.

Figure 6:
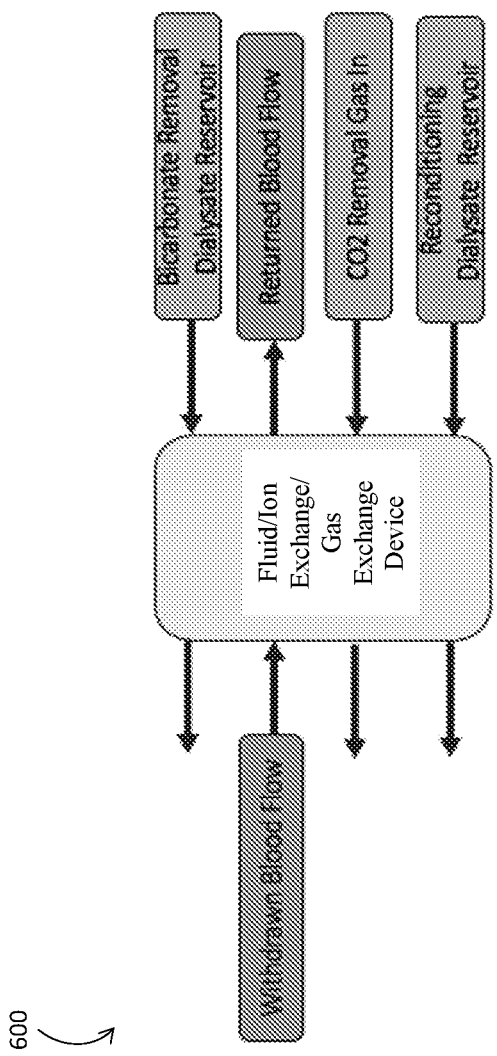
FIG. 6 is a block diagram illustrating a system for carbon dioxide removal from patient's blood, in accordance with some embodiments.

FIG. 6 illustrates schematically a system 600 including a hybrid device in accordance with the described techniques, shown as a fluid/ion exchange/gas exchange device 602. Blood withdrawn from the patient ("Withdrawn blood flow") is passed through the fluid/ion exchange/gas exchange device 602 and treated using a sweep gas ("CO2 removal gas"), a dialysate provided from a dialysate source ("Bicarbonate Removal Dialysate Reservoir"), and a reconditioning fluid ("Reconditioning Dialysate Reservoir"). After dissolved $CO_2$ and bicarbonate are removed from the blood, the treated blood is delivered back to the patient's vascular system ("Returned Blood Flow").

A hybrid cartridge in accordance with the described techniques, which can operate to remove both dissolved $CO_2$ (e.g., through gas exchange component(s)) and bicarbonate (e.g., through fluid/ion exchange component(s)) are removed from blood passed therethrough, can be configured in various ways. FIGS. 7A and 7B illustrate one embodiment of an example of a hybrid cartridge 702 that has a fully cannulated generally cylindrical body 702a having an inner cavity 704 extending between first and second ends 706a, 706b of the cartridge body 702a. The inner cavity 704 is configured to receive therein first and second membrane components. FIG. 7A shows that the cartridge body 702a includes a fluid inlet 708 formed adjacent to the first end 706a and a fluid outlet 710 formed adjacent to the first end 706a of the cartridge body 702a. As shown, the fluid inlet 708 and the fluid outlet 710 are formed perpendicular to a longitudinal axis A2 of the cartridge body 702a extending between the first and second ends 706a, 706b thereof. In other embodiments, however, the fluid inlet 708 and the fluid outlet 710 can be formed in other ways with respect to the longitudinal axis A2 of the cartridge body 702a, including differently from one another. In use, blood obtained from a patient can be delivered through the fluid inlet 708, passed through the cartridge body 702a, along the longitudinal axis A2, towards the fluid outlet 710. A sweep gas and a dialysate can be passed through the cartridge body 702a in a direction that is opposite or along an axis angled with respect to the axis A2, which can depend on a configuration of membrane components housed within the cartridge body 702a.

In the example shown in FIGS. 7A and 7B, the hybrid cartridge 702 includes a first end cap 750 configured to removably couple to the first end 706a of the cartridge body 702a, and a second end cap 752 configured to removably couple to the second, opposite end 706b of the cartridge body 702a. The second end cap 752 includes first and second inlets 716, 722, and the first end cap 750 includes first and second outlets 720, 726. In this embodiments the inlets and outlets are in the form of hollow tubular members having passages that communicate with the interior cavity 704 of the cartridge body 702a. However, the inlets and outputs can have other configurations, as the described embodiments are not limited in this respect. The first inlet 716 and the first outlet 720 are configured to deliver and remove, respectively, a first sweep component, such as, e.g., a sweep gas. The second inlet 722 and the second outlet 726 are configured to deliver and remove, respectively, a second sweep component, such as, e.g., a dialysate. It should be appreciated that, depending on a configuration of the cartridge, the first and second sweep components can also be a dialysate and gas, respectively. It should also be appreciated that the inlets and outlets can be positioned in other ways with respect each other, and that a "top" and "bottom" inlets and outputs, as shown in FIGS. 7A and 7B, can be reversed, such as "top" components become "bottom" components, and vice versa.

The first and second end caps 750, 752 are configured to couple to the ends of the cartridge body 702a, for example, by being threadably or otherwise engaged with the respective ends in an air-tight manner. Additionally or alternatively, as shown in FIGS. 7A and 7B, the inner surface of the cartridge body 702a adjacent to the first and second ends 706a, 706b can have inner threads configured to releasably engage with corresponding threads 707a, 707b formed on the outer surfaces of the cartridge body at the first and second ends 706a, 706b. It should be appreciated that the end caps can be configured to engage with the cartridge body in other suitable ways.

FIGS. 8A to 8D shows an example of an end cap 850 of a cartridge, such as, e.g., any of the end caps 750, 752 shown in FIGS. 7A and 7B. FIG. 7B shows that the end cap 850 has first and second inlets 816, 822 coupled to an outer surface 854 thereof. First and second outlets can be formed on an end cap in a similar manner. The first and second inlets 816, 822 can be formed along the same plane, as shown in FIG. 8C. However, other configurations can be implemented. FIG. 8D shows that an inner surface 856 of the end cap 850 has a thread 858 formed thereon, which can be configured to releasably engage with a corresponding thread (e.g., thread 707a or 707b of FIGS. 7A and 7B) formed on the cartridge body.

Figure 9:
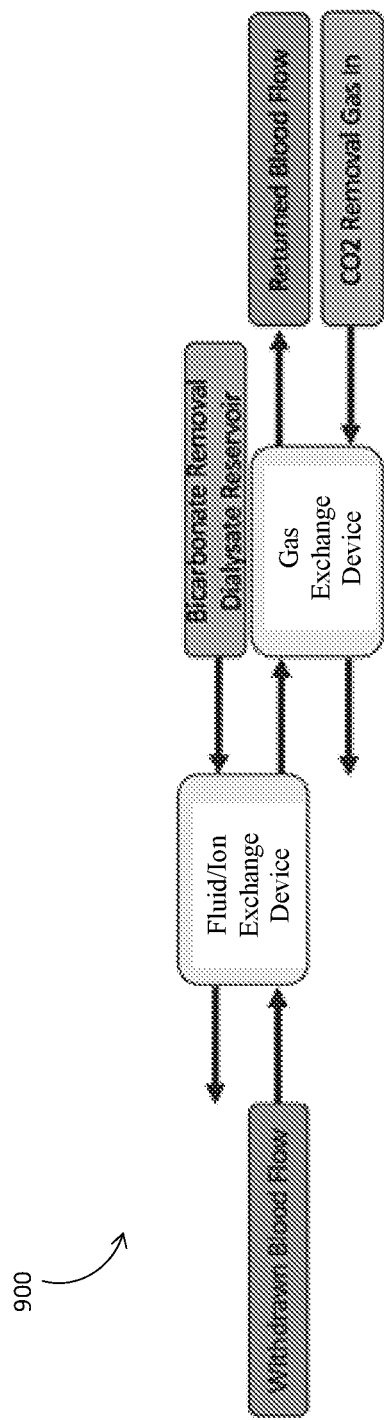
FIG. 9 is a block diagram illustrating an example of a system for carbon dioxide removal from patient's blood, in accordance with some embodiments.

Configurations of first and second membrane components of a system in accordance with the described techniques can vary in many ways. The first and second membrane components can be configured as modular components configured to be coupled within a system in accordance with the described techniques in various ways. For example, in some embodiments, at least one first membrane component ("gas exchange" component(s)) can be coupled in series with at least one second membrane component ("Fluid/Ion exchange" component(s)). FIG. 9 illustrates an example of a system 900 having a fluid/ion exchange membrane component and a gas exchange membrane component coupled in series with one another. In this example, the blood acquired from a patient is first treated via a fluid exchange membrane component ("Fluid/Ion Exchange device") and is then treated via a gas exchange membrane component ("Gas Exchange device"). The gas exchange and fluid/ion exchange membrane components can have the same or different configurations. For example, each of the membrane components can include both first and second fiber components as described herein.

Figure 10:
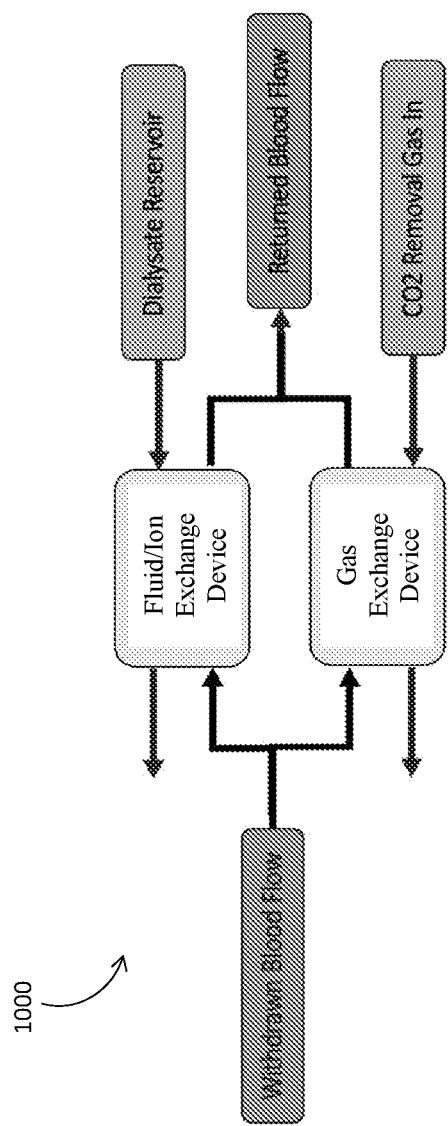
FIG. 10 is a block diagram illustrating another example of a system for carbon dioxide removal from patient's blood, in accordance with some embodiments.
Figure 11:
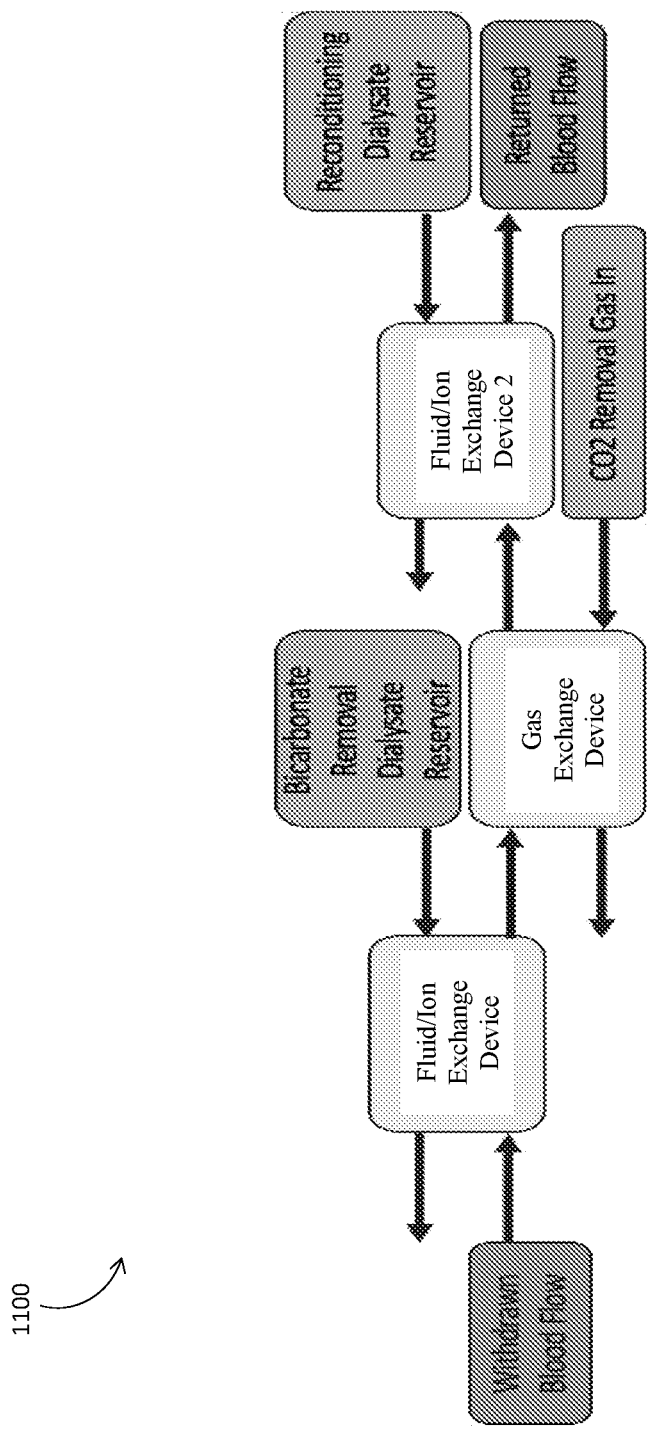
FIG. 11 is a block diagram illustrating another example of a system for carbon dioxide removal from patient's blood, in accordance with some embodiments.
Figure 12:
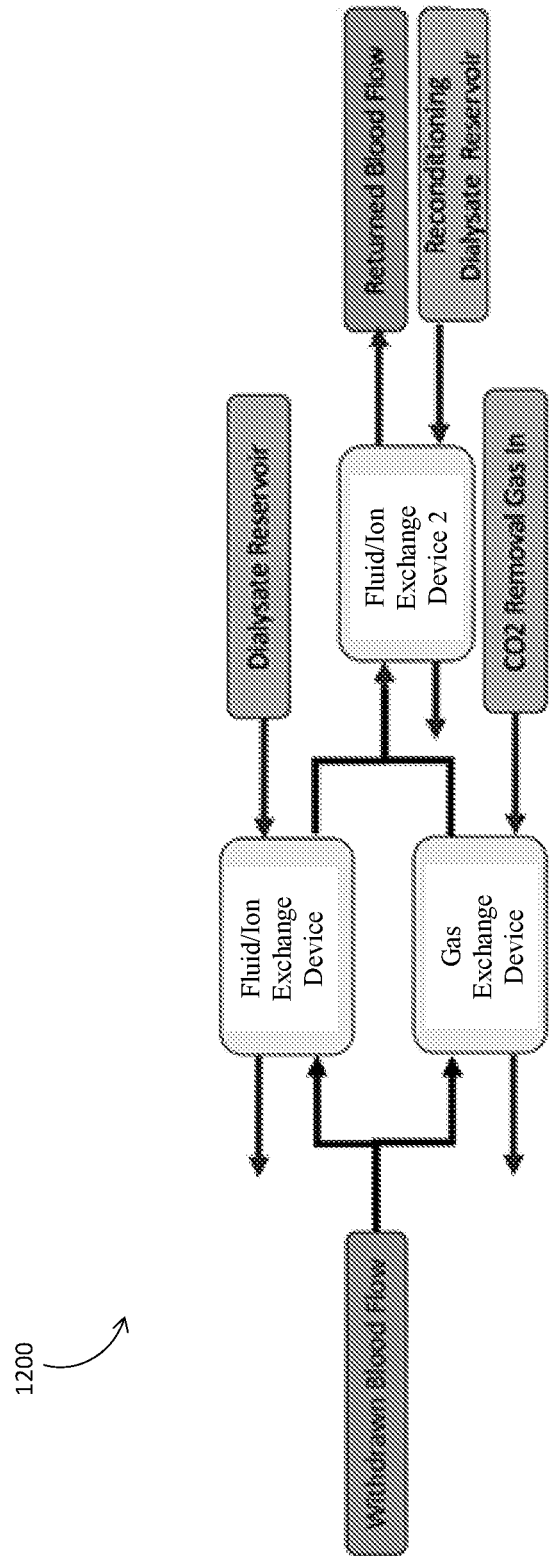
FIG. 12 is a block diagram illustrating another example of a system for carbon dioxide removal from patient's blood, in accordance with some embodiments.

FIG. 10 illustrates an example of a system 1000 having a gas exchange membrane component and a fluid/ion exchange membrane component coupled in parallel with one another. In some embodiment, more than one first membrane component and/or more than one second membrane component can be used. For example, FIG. 11 illustrates an example of a system 1100 including, among other components, a second fluid/ion exchange component ("Fluid/Ion Exchange device 2") configured to treat blood via a post-exchange membrane having a reconditioning fluid being passed therethrough. FIG. 12 illustrates an example of a system 1200, also including a second fluid/ion exchange component ("Fluid/Ion Exchange device 2"), having a configuration alternative to a configuration of FIG. 1100. As shown in FIG. 12, gas exchange and fluid/ion exchange membrane components are coupled in parallel to one another. Any other configurations of a system for dissolved carbon dioxide/bicarbonate removal from blood or other fluid can be implemented. It should be appreciated that the components shown as "gas exchange" components in FIGS. 9-12 can be configured such that they do not perform oxygenation but only remove gaseous $CO_2$ from fluids, such as, e.g., blood, passing therethrough.

In the illustrated embodiments, a dialysate used to remove bicarbonate from blood can have various compositions. In some embodiments, one or both of the first and second ultrafiltration membrane components includes an ultrafiltration membrane, which can be a semi-permeable ultrafiltration membrane. The ultrafiltration membrane includes pores and it can be permeable to species that are smaller than its pore size. Selective transport of species through the membrane is driven by a composition of a sweep fluid, which can also be referred to as a dialysate.

Transport of species across the membrane can be defined using the Fick's laws of diffusion postulating that a transport rate of a species across a membrane is determined by an area of the membrane, membrane permeability (function of diffusivity), and the concentration gradient of the species. In some implementations, an area of an ultrafiltration membrane is not changeable and the membrane permeability is similar for species of a similar size. In other implementations, additionally or alternatively, an ultrafiltration membrane can have a more selective permeability that is dependent on various species characteristics such as, e.g., charge. In these and other scenarios, membrane selectivity is dependent on a composition of a dialysate for species that have a size that allows then to pass through membrane pores or other structures of the membrane that can pass species therethrough. In some embodiments, an ultrafiltration membrane is not permeable for most cellular and protein components of blood but is permeable to the major ionic species (e.g., sodium, potassium, chloride, and bicarbonate) and glucose included in blood. Glucose is not charged, and its content in a fluid can be determined using a variety of techniques, including a basic metabolic panel blood test. Sodium, potassium, chloride, and bicarbonate are charged species, and their presence and relationship in a fluid can create a chemical gradient in accordance with Fick's laws of diffusion. Movement of any charged species may also result in an electrical gradient induced by charge imbalances that create electric potentials as determined by Coulomb's law. To avoid undesirable charge imbalances (which can increase electrical potentials), selective mass filtration of species is performed so that to maintain charge balance in both the blood and the dialysate, while preventing undesirable buildup of electrical potentials. Charge balance can be maintained by ensuring that every charge is allowed to be coupled with movement of another charge.

In some embodiments, as mentioned above, the dialysate includes zero bicarbonate. It is desired to maintain blood electrical neutrality, along with the capture of carbon dioxide. Suitable membrane transport of bicarbonate may also increase transport of other ions in the blood to maintain electrical neutrality. When this causes a net movement of non-bicarbonate ion into the dialysate, a so-called off-target capture takes place. Because of this, a balance between suitable bicarbonate and off-target capture need to be achieved. Off-target capture is undesirable and necessary to account for blood electrical neutrality. A dialysate having electrolyte molarity similar to blood molarity, e.g., greater than 135 mM, can promote counter-transport of ions (movement of chloride ion into blood), resulting in lower off-target capture. Low dialysate concentrations can promote co-transport of sodium ions out of the blood with higher degree of off-target capture. Both are present in order to maintain electrical neutrality with an electrical flux being induced by bicarbonate transportation.

In some embodiments, the described systems, devices, and methods enable a hybrid "low-flow" extracorporeal device that is less invasive and requires less clinical expertise than existing extracorporeal strategies to treat HRF with the aim of being able to be more widely deployed. Specifically, increased efficiency of removal of high carbon dioxide load from the blood may allow lower blood flow rates, and reduced bore size of cannulae used for extracorporeal treatment. Impaired ventilation leading to inadequate respiratory removal of dissolved $CO_2$, can be more efficiently treated by using a custom dialysate to promote $HCO_3^-$ filtration, which allows for removal of >50% of the body's production of $CO_2$ through removal of a small fraction of the body's total $HCO_3^-$. However, isolated removal of $HCO_3^-$ affects the body's acid-base balance. As a result, a hybrid device approach that utilizes an integrated fluid/ion exchange/gas exchange system that may be compatible with commercial dialysis circuits with balanced $HCO_3^-$ and $CO_2$ removal can be used to offset substantial changes in blood acid-base. Correction for less substantial changes in blood acid-base can be corrected using additional solutes including specific organic bases such as, for example, monoethanolamine (MEA). It should be appreciated that, although some embodiments described herein are directed towards removal of bicarbonate and $CO_2$ in the setting of HRF, the described techniques can be applied to other blood or bodily fluid requiring removal or addition of specific constituents while maintaining homeostatic conditions.

In some embodiments, the system can include the following components: (1) target solute membrane filter, (2) gas exchange fibers, and (3) homeostatic solute membrane filter. The target solute membrane filter operates with selective membrane filter with specially designed counter flow solutions for targeted removal of bicarbonate and other pertinent ions from the blood. Filtration of bicarbonate and other pertinent ions can occur with counter transport exchange or co-transport exchange to maintain electrical neutrality. Blood homeostasis is maintained by simultaneous or serial removal of gaseous $CO_2$ through gas exchange fibers. This removal of gaseous $CO_2$ can occur in parallel, series, or integrated with the bicarbonate filtration step such that gas exchange fibers run adjacent to fibers of filtration membranes configured for bicarbonate removal. Additional adjustment to filtered blood can occur with a homeostatic solute membrane filter. This filter can be used to add components to the filtered blood prior to recirculation to the body. This can include restoring primary electrolytes such as sodium, potassium, and chloride or additional pH adjustment through the addition of biocompatible organic bases, such as, e.g., monoethanolamine (MEA).

In some embodiments, an extracorporeal circuit is provided that is configured to remove blood from a subject's body at low flow levels, perform targeted removal of bicarbonate ion from blood flow, and perform targeted removal of $CO_2$ gas from blood flow. The extracorporeal circuit can also be configured to recondition the blood flow using a dialysate fluid to rebalance ions and pH. The reconditioned blood is then returned to the subject's body. The low flow levels can be in the range from about 0 to about 400 mL/min.

In some embodiments, the extracorporeal circuit has components comprising a dialysate based filtration component comprising a counter exchange ultrafiltration membrane, a dialysate fluid suitable for removal of bicarbonate ion; a gas exchange component comprising a counter gas flow suitable for removal of $CO_2$ gas from blood flow; and a dialysate based filtration component comprising a counter exchange ultrafiltration membrane, and a dialysate fluid suitable for addition of biocompatible solutes or salts.

The extracorporeal circuit can vary in different ways. For example, each component can be operated and manufactured separate from each other component(s) with none, one, or more than one replicates iterations of each component in a given extracorporeal circuit. Each component can be configured in series such that the output of each component is the input of the following component in different possible configured orders. In some aspects, each component can be configured in parallel with other components such that input blood flow can be separated into different flow lines to travel to different components and reconstituted prior to recirculation to the body. In some aspects, each component can be configured into different subsystems that are a combination of different serial or parallel configurations, with different subsystems combined in serial or parallel configuration. In some aspects, each component can be integrated with one another such that they form a single component with dialysate based filters that run directly in parallel and exposed to the same blood flow at a given time as oxygenator-based fibers used for gas exchange.

In some embodiments, the system or a portion thereof can be packaged into a single cartridge that can be adapted to be used with commercial kidney dialysis systems. The system can include various components such as, e.g., a pH meter which can be disposed at input or output (i.e., before or after) of any components, in order to adjust operation of a dialysate filtration component used for addition of biocompatible solvents. In some embodiments, additionally or alternatively, a feedback control effector of dialysate filtration is modulated by changing a flow rate of the dialysate component. In some embodiments, additionally or alternatively, a feedback control effector for $CO_2$ gas filtration is modulated by changing the flow rate of the sweep gas either automatically or via user input.

The dialysate filtration components can use dialysate fluids that are suitable for counter transport to maintain electrical neutrality. In some embodiments, the dialysate filtration components may use dialysate fluids that are suitable for unidirectional co-transport to maintain electrical neutrality. In some embodiments, the dialysate filtration components use dialysate fluids that contain primary plasma ions to add ions to the blood to restore normal ionic concentrations in blood.

In some embodiments, the dialysate filtration components use dialysate fluids that contain biocompatible organic base(s) to be added to the blood to correct pH. The biocompatible organic base can comprise, for example, monoethanolamine (MEA).

In the described embodiments, the ultrafiltration membranes can be selective for specific species by size, charge, or molecular configuration.

In some embodiments, the described systems, devices, and methods provide for treatment or prevention of a respiratory failure. In some embodiments, the described systems, devices, and methods provide for treatment or prevention of hypoxemia. In some embodiments, the described systems, devices, and methods provide for treatment or prevention of hypercapnia.

The respiratory failure of the present invention can be, in some embodiments, Type I or Type II.

Type 1 respiratory failure is defined as a low level of oxygen in the blood (hypoxemia) without an increased level of carbon dioxide in the blood (hypercapnia), and the $P_aCO_2$ may be normal or low. It is typically caused by a ventilation/perfusion (V/Q) mismatch; the volume of air flowing in and out of the lungs is not matched with the flow of blood to the lungs. The basic defect in type 1 respiratory failure is failure of oxygenation characterized by: decreased (<60 mmHg (8.0 kPa)) $P_aO_2$; normal or decreased (<50 mmHg (6.7 kPa)) $P_aCO_2$; and increased $P_AaO_2$. In various embodiments, the described systems, devices, and methods reverse any of these parameters.

In various embodiments, the Type 1 respiratory failure is caused by, for example, conditions that affect oxygenation such as: low ambient oxygen (e.g., at high altitude), ventilation-perfusion mismatch (e.g., pulmonary embolism), alveolar hypoventilation (e.g., in acute neuromuscular disease), diffusion problems (e.g. in pneumonia or ARDS) and shunts (e.g., right to left shunt). In various embodiments, the described systems, devices, and methods treat a subject afflicted with any of these causes.

Type 1 respiratory failure is defined as hypoxemia ($P_aO_2$<8 kPa) with hypercapnia ($P_aCO_2$>6.0 kPa).

The basic defect in type 2 respiratory failure is characterized by: decreased (<60 mmHg (8.0 kPa)) $P_aO_2$, increased (>50 mmHg (6.7 kPa)) $P_aCO_2$, normal $P_{A-a}O_2$, and decreased pH. In various embodiments, the described systems, devices, and methods reverse any of these parameters.

Type 2 respiratory failure is caused by, for example, inadequate alveolar ventilation and both oxygen and carbon dioxide are affected. Type 2 is defined as the buildup of carbon dioxide levels ($P_aCO_2$) that has been generated by the body but cannot be eliminated. The underlying causes include, without limitation: increased airways resistance (e.g., COPD, asthma, suffocation), reduced breathing effort (e.g., drug effects, brain stem lesion, extreme obesity), decrease in the area of the lung available for gas exchange (e.g., in chronic bronchitis), neuromuscular problems (e.g., Guillain-Barré syndrome, motor neuron disease), and deformed (kyphoscoliosis), rigid (ankylosing spondylitis), or flail chest. In various embodiments, the described systems, devices, and methods treat a subject afflicted with any of these causes.

In embodiments, the subject who is treated in the present invention is afflicted with respiratory failure as presented by, for example, increased respiratory rate, abnormal blood gases (e.g., hypoxemia, hypercapnia, or both), and evidence of increased work of breathing.

In embodiments, the described systems, devices, and methods provide for restoration of normal, or about normal, partial pressure reference values of oxygen and/or carbon dioxide in the subject. For instance, the described systems, devices, and methods provide for restoration of oxygen $PaO_2$ to more than about 80 mmHg (11 kPa) and/or carbon dioxide $PaCO_2$ to less than about 45 mmHg (6.0 kPa).

In some embodiments, the described systems, devices, and methods provide for treatment or prevention of a HRF, e.g., characterized by an increased plasma concentration of carbon dioxide in the setting of inadequate ventilation. In some embodiments, the described systems, devices, and methods provide for treatment or prevention impairments in respiratory drive (e.g., stroke or obesity hypoventilation), decreased neuromuscular function (e.g., muscular dystrophy or amyotrophic lateral sclerosis), and lung disease (e.g., COPD or interstitial lung disease).

In some embodiments, the described systems, devices, and methods provide for treatment or prevention of COPD. In some embodiments, the described systems, devices, and methods reduce one of more symptoms of COPD, such as shortness of breath and cough with sputum production. In some embodiments, the described systems, devices, and methods provide for treatment or prevention of severe COPD patients with exacerbation.

In some embodiments, the described systems, devices, and methods are used in conjunction with one or more phosphodiesterase (PDE)-selective inhibitors, e.g., roflumilast (DAXAS, DALIRESP), cilomilast (ARIFLO), or tetomilast. In some embodiments, the described systems, devices, and methods ameliorate the development of tolerance against roflumilast, cilomilast, or tetomilast.

In some embodiments, the described systems, devices, and methods provide for treatment or prevention of an ARDS. In some embodiments, the described systems, devices, and methods reduce one of more symptoms of ARDS, such as, without limitation, shortness of breath, rapid breathing, and bluish skin coloration.

In some embodiments, the present subject presents with symptoms such that he or she is suited for treatment with of non-invasive mechanical ventilator support (e.g., Bilevel Positive Airway Pressure (BiPap)). In some embodiments, the present subject presents with symptoms such that he or she is suited for treatment with intubation and full mechanical ventilation. In some embodiments, the present systems, devices, and methods spare a subject from treatment or reduce duration of treatment with non-invasive mechanical ventilator support (e.g., BiPap). In some embodiments, the present systems, devices, and methods spare a subject from treatment or reduce duration of treatment with intubation and full mechanical ventilation.

In some embodiments, an extracorporeal system for removing carbon dioxide from a fluid is provided. The system can include a cartridge body, a first membrane component, a second membrane component, a first inlet in fluid communication with the first membrane, a first outlet in fluid communication with the first membrane component, a second inlet in fluid communication with the second membrane component, and a second outlet in fluid communication with the second membrane component. The cartridge body can have a cavity, a longitudinal axis extending between first and second ends of the body, a fluid inlet adjacent to the first end, and a fluid outlet adjacent to the second end.

The first membrane component disposed within the cavity can be configured to remove gaseous carbon dioxide from the fluid passing from the fluid inlet in a first direction towards the fluid outlet. The second membrane component disposed within the cavity can be configured to remove bicarbonate from the fluid passing between the fluid inlet and the fluid outlet. The first inlet in fluid communication with the first membrane component is configured to deliver a sweep gas to the first membrane such that the sweep gas is passed through the first membrane in a second direction, and the first outlet in fluid communication with the first membrane component is configured to receive the sweep gas passed through the first membrane. The second inlet in fluid communication with the second membrane component can be configured to deliver a dialysate to the second membrane such that the dialysate is passed through the second membrane in a third direction, and the second outlet in fluid communication with the second membrane component can be configured to receive the dialysate passed through the second membrane.

In the system in accordance with the described techniques, the fluid being treated can be blood, blood plasma, or any other fluid. In some embodiments, the fluid inlet receives the fluid at a flow rate in a range from about 0 mL/min to about 350 mL/min (e.g., less than about 350 ml/min, or less than about 300 ml/min, or less than about 250 ml/min, or less than about 200 ml/min, or less than about 150 ml/min, or less than about 100 ml/min, or less than about 90 ml/min, or less than about 80 ml/min, or less than about 70 ml/min, or less than about 60 ml/min, or less than about 50 ml/min, or less than about 40 ml/min, or less than about 30 ml/min, or less than about 25 ml/min).

In some embodiments, at least one of the second and third directions can be substantially parallel to the first direction.

In some embodiments, the extracorporeal system can include a third membrane component providing an interface between the fluid and a reconditioning fluid. The reconditioning fluid can have a composition configured to regulate an ionic composition and acidity of the fluid. The third membrane component can be disposed in the system in various ways. For example, in some embodiments, the third membrane component can be positioned such that the fluid is brought in contact with the third membrane component after the gaseous carbon dioxide and the bicarbonate are removed from the fluid. In some embodiments, the third membrane component is positioned in the cartridge body. In other embodiments, the third membrane component is positioned outside of the cartridge body. The reconditioning fluid can have various compositions. For example, in some embodiments, it can include a biocompatible organic base, which can be, e.g., monoethanolamine (MEA). Additionally or alternatively, in some embodiments, the reconditioning fluid can include at least one of sodium chloride, bicarbonate, potassium, calcium, phosphate, sulfate, and magnesium.

The first and second membrane components can have various configurations. In some embodiments, the first membrane component can be in the form a first plurality of fibers extending between the first and second ends and configured to receive the sweep gas passing therethrough. When the sweep gas passes through the first plurality of fibers, gaseous carbon dioxide transfers from the fluid into the sweep gas. The second membrane component can be in the form of a second plurality of fibers extending between the first and second ends and configured to receive the dialysate passing therethrough. When the dialysate passes through the second plurality of fibers, bicarbonate transfers from the fluid into dialysate. The fluid can be passed through the cartridge body such that it is brought in contact with an exterior surface of the first and second membrane components, such that the sweep gas and dialysate are separated from the blood by the first and second membrane components, respectively.

The first and second plurality of fibers can have various configurations (including different configurations, and they can be disposed in the cartridge in various ways. For example, in some embodiments, the first plurality of fibers are intermingled with the second plurality of fibers. In some embodiments, the first plurality of fibers are substantially parallel to the second plurality of fibers.

In some embodiments, the first plurality of fibers are disposed in a first area of the cavity of the cartridge body and the second plurality of fibers are disposed in a second area of the cavity of the cartridge body, the second area being different than the first area. In some embodiments, the first plurality of fibers and the second plurality of fibers are disposed at an angle to the longitudinal axis of the cartridge body, with the first plurality of fibers being disposed at an angle with respect to the second plurality of fibers.

In some embodiments, the system includes a controller having circuitry configured to acquire measurements of at least one parameter characterizing a state of at least one of the fluid, the dialysate, and the sweep gas as the fluid passes through the cartridge body, and to control, in response to the acquired measurements, at least one of a flow rate of the fluid, a flow rate of the dialysate, and a content of the dialysate. In some embodiments, the at least one parameter comprises electrolyte content of the fluid, and wherein the system comprises at least one electrolyte sensor configured to measure the electrolyte content as the fluid passes through the cartridge body. In some embodiments, the at least one parameter comprises pH values of the fluid, and the system includes at least one pH meter configured to acquire the pH values of the fluid and/or other substances. In some embodiments, the at least one parameter comprises a flow rate of the sweep gas and a content of the sweep gas.

In some embodiments, the system or some of its components (e.g., the cartridge) are adapted for use with a kidney dialysis system.

In some embodiments, the dialysate is a liquid composition suitable for counter transport to maintain electrical neutrality. In some embodiments, the dialysate is a liquid composition suitable for unidirectional co-transport to maintain electrical neutrality. In some embodiments, the dialysate comprises zero bicarbonate and at least one of sodium, chloride, potassium, calcium, phosphate, sulfate, and magnesium. In some embodiments, additionally or alternatively, the dialysate comprises at least one biocompatible organic base, which can be, e.g., monoethanolamine (MEA) or another compound(s).

In some aspects, a method for removing gaseous carbon dioxide and bicarbonate from fluids is provided. The method can include removing a fluid from a patient via a cannula in fluid communication with the patient's body, and causing the fluid to enter an extracorporeal housing comprising a first membrane component and a second membrane component such that the fluid is placed in contact with exterior surfaces of at least one of the first and second membrane components. The method further includes passing a sweep gas through the first membrane component to cause gaseous carbon dioxide to transfer from the fluid into the sweep gas, passing a dialysate through the second membrane component to cause bicarbonate to transfer from the fluid into the dialysate, and causing the fluid to exit the housing after the fluid has passes through the housing such that the gaseous carbon dioxide and bicarbonate are removed from the fluid.

The method can vary in different ways. For example, passing the sweep gas through the first membrane component and passing the dialysate through the second membrane component can be performed substantially simultaneously. As another example, the sweep gas can be passed through the first membrane component before the dialysate is passed through the second membrane component. As yet another example, the dialysate can be passed through the second membrane component before the sweep gas is passed through the first membrane component. In some embodiments, the fluid is blood that is removed from the patient at a non-zero flow rate smaller than 400 ml/min.

In some aspects, a method for treating a hypercarbic respiratory failure (HRF) is provided. In some embodiments, the method includes selecting a patient in need of HRF treatment, drawing blood from the patient at a rate smaller than 400 ml/min, and subjecting the blood to at least one membrane configured to remove gaseous $CO_2$ and bicarbonate from the blood to bring a carbon dioxide level in the blood to a baseline level.

The method can vary in different ways. For example, the gaseous $CO_2$ and bicarbonate can be removed substantially simultaneously from the blood. As another example, the at least one membrane can include first and second membrane components, and the method can involve passing a sweep gas through the first membrane component and passing a dialysate through the second membrane component.

In some embodiments, the dialysate has zero bicarbonate and a composition of dialysate is such that charge neutrality is maintained at least across the second membrane component. In some embodiments, the composition of the dialysate is selected based on an initial sodium concentration and an initial chloride concentration of the blood, wherein the initial sodium concentration and the initial chloride concentration are measured before the blood is subjected to the at least one membrane. In some embodiments, when the initial sodium concentration is greater than a threshold sodium concentration, a sodium concentration of the dialysate can be selected to be smaller than the initial sodium concentration, and a chloride concentration of the dialysate can be selected to be approximately the same as the initial chloride concentration. When the initial sodium concentration is smaller than the threshold sodium concentration, a sodium concentration of the dialysate can be selected to be approximately the same as the initial sodium concentration, and a chloride concentration of the dialysate can be selected to be greater than the initial chloride concentration.

In some embodiments, the method can further include adjusting the composition of the dialysate based on measurements of electrolyte content of at least one of the blood and the dialysate as the blood is being subjected to the at least one membrane, so as to maintain the charge neutrality.

In some aspects, a method for treating a hypercarbic respiratory failure (HRF) is provided. In some embodiments, the method includes selecting a patient in need of HRF treatment, drawing blood from the patient at a rate smaller than 400 ml/min, subjecting the blood to a first membrane component configured to remove gaseous $CO_2$ from the blood, the first membrane component having a sweep gas passing therethrough, and subjecting the blood to a second membrane component configured to remove bicarbonate from the blood, the second membrane component having a bicarbonate removal liquid passing therethrough. The bicarbonate removal liquid can have zero bicarbonate and sodium and chloride at concentrations that allow maintaining electrical charge neutrality at the second membrane component. In some embodiments, the sweep gas has zero gaseous CO2.

Regardless of the specific configuration of the device and system in accordance with the described techniques, the cannula used to withdraw blood from the patient can have a reduced diameter—for example, it can have an outer diameter in a range from about 8 Fr to about 13 Fr. The fluid can be removed from the patient at a non-zero rate less than about 400 ml/min.

In some embodiments, a method for treating a hypercarbic respiratory failure (HRF) is provided that includes selecting a patient in need of HRF treatment, drawing blood from the patient at a rate smaller than 400 ml/min, and subjecting the blood to at least one membrane configured to remove gaseous $CO_2$ and bicarbonate from the blood to bring a carbon dioxide level in the blood to a baseline level. In some embodiments, the gaseous $CO_2$ and bicarbonate can be removed substantially simultaneously from the blood. In other embodiments, the gaseous $CO_2$ is removed from the blood before the bicarbonate is removed from the blood, or the bicarbonate is removed from the blood before the gaseous $CO_2$ is removed from the blood.

In the methods in accordance with some embodiments, the at least one membrane comprises first and second membrane components, and the method can comprise passing a sweep gas through the first membrane component and passing a dialysate (or bicarbonate removal fluid) through the second membrane component.

The methods described herein can utilize any of the systems or devices described herein. For example, the method can be implemented in system 100 (FIG. 1), system 100' (FIG. 2), or in any other system in accordance with the described techniques. The methods can be used to treat or prevent various conditions, non-limiting examples of which include a respiratory failure (Type I or Type II), hypoxemia, or hypercapnia. The methods provide for treatment or prevention of a HRF, impairments in respiratory drive (e.g., stroke or obesity hypoventilation), decreased neuromuscular function (e.g., muscular dystrophy or amyotrophic lateral sclerosis), and lung disease (e.g., COPD or interstitial lung disease). The methods can also provide for treatment or prevention of COPD with any of the systems or devices described herein.

In some embodiments, the described methods are used in conjunction with one or more phosphodiesterase (PDE)-selective inhibitors, e.g., roflumilast (DAXAS, DALIRESP), cilomilast (ARIFLO), or tetomilast. In some embodiments, the described systems, devices, and methods ameliorate the development of tolerance against roflumilast, cilomilast, or tetomilast.

A "subject" is a mammal, e.g., a human (e.g., a female or a male human), mouse, rat, guinea pig, dog, cat, horse, cow, pig, or non-human primate, such as a monkey, chimpanzee, baboon or rhesus, and the terms "subject" and "patient" are used interchangeably herein.

This invention is further illustrated by the following non-limiting examples.

Examples

The inventors conducted experiments using a benchtop model, to reduce loss of sodium, the most abundant ion in the body, while maintaining sufficiently high levels of $CO_2$ removal to support the subject in HRF. Animal model experiments, discussed below, were used to create a suitable transport mode for electrical neutrality, to determine a dialysate composition for use in the described devices, systems, and methods. In the experiments described below, a device prototype was used that included components based on dialysate and oxygenator technology for concurrent liquid-liquid and liquid-gas filtration. In these preliminary prototype, the dialysate and gas exchange components were coupled and operated in series.

Benchtop Experiments

Figure 13:
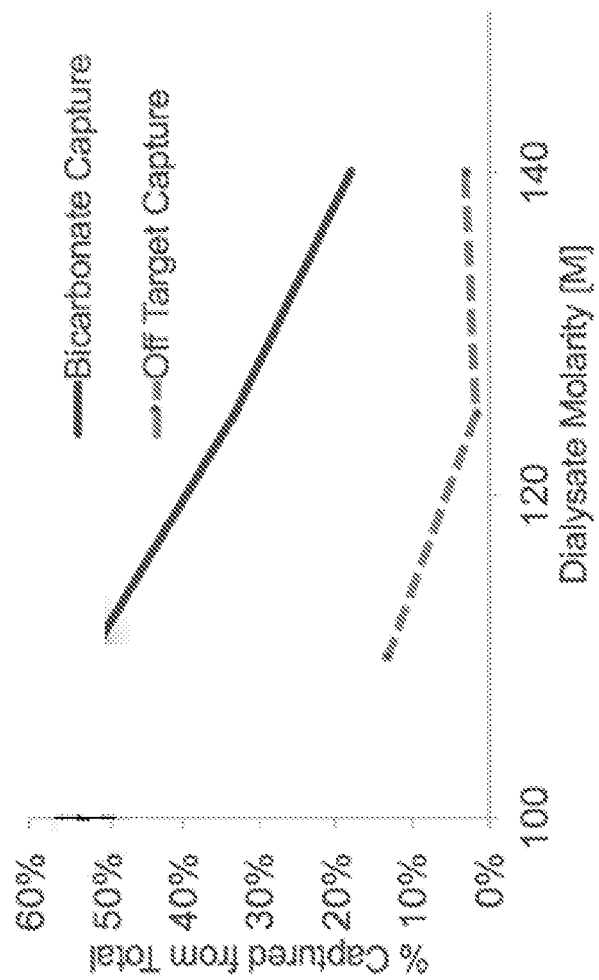
FIG. 13 illustrates bicarbonate capture and off-target ion capture efficiencies at different dialysate molarities, as determined during in vitro experiments.

Assuming a maximum $CO_2$ production rate of 536 mmoL/hr (in an adult active male), an effective membrane capture rate of 37% is estimated to be necessary for therapeutic effect. As shown in FIG. 13, this value was reached using the benchtop testing at low-flow conditions of <400 mL/min.

Animal Experiments

The prototype device was tested in a series of four acute hypercarbic pig models. To induce hypercarbic conditions, ventilator settings were changed to 4-5 breaths per minute and a positive end expiratory pressure was used to maintain adequate oxygenation. Serial blood gas analyses, using an OPTI CCA device, was performed at 10 minute intervals to titrate to effect and indicate a stable level of hypercarbia. Once a peak disease condition was achieved, the prototype device was turned on using a 125 mM concentration ionic solution as a sweep liquid containing sodium, potassium, and chloride ions that was determined to be suitable based off of benchtop testing characterization. The device was connected using a 13 FR dialysis catheter in venous access for withdrawal and return of blood. Flows were maintained at 248 mL/min and pumped using standard cardiopulmonary bypass roller pumps. Serial measurements of arterial, venous pre-device, and venous-post device were taken at set intervals. After more than an hour of device operation, the device operation was discontinued, and the animal was euthanized in accordance with standard protocols. There were no acute events during any of the animals.

Figure 14:
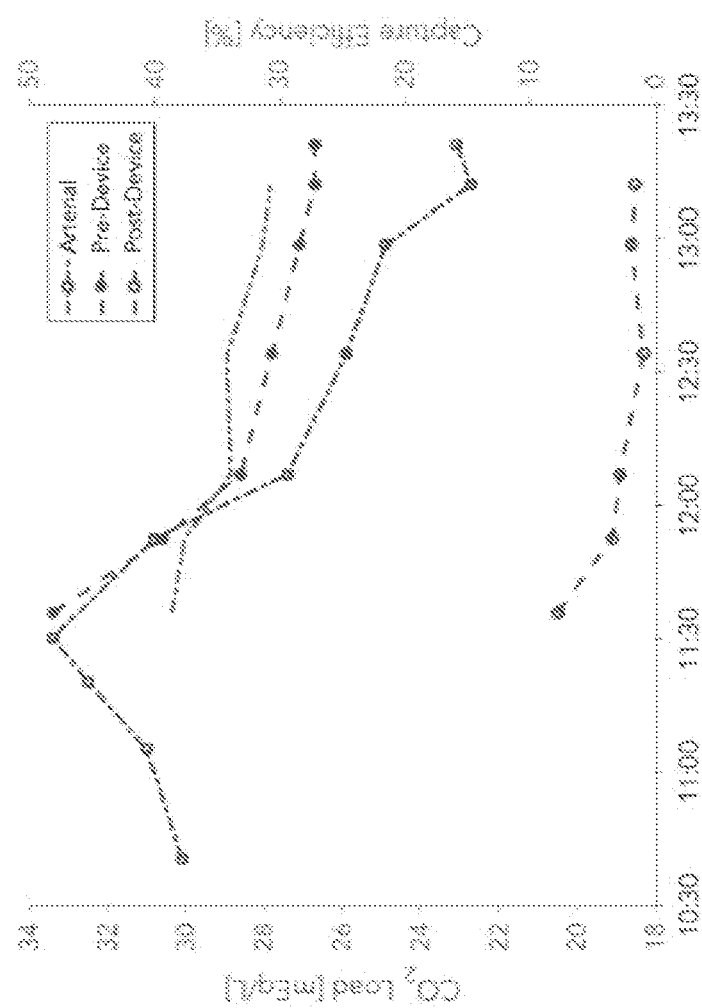
FIG. 14 illustrates values obtained using a blood gas analysis for $CO_2$ load during a time course of a single-animal experiment. Capture efficiency (%) is determined from measurements of $CO_2$ loads (mEq/L) acquired over a time period from about 10:45 am to about 13:20 pm, with serial measurements in arterial blood, venous blood prior to the treatment, and venous blood after the treatment taken at predetermined intervals. The capture efficacy was determined to be similar to capture efficacy determined during benchtop testing, and a weak relationship with $CO_2$ load was observed. For reference, at time point 13:00, from bottom to top, the curves with circle plot indicators are: post-device, arterial, and pre-device.
Figure 15:
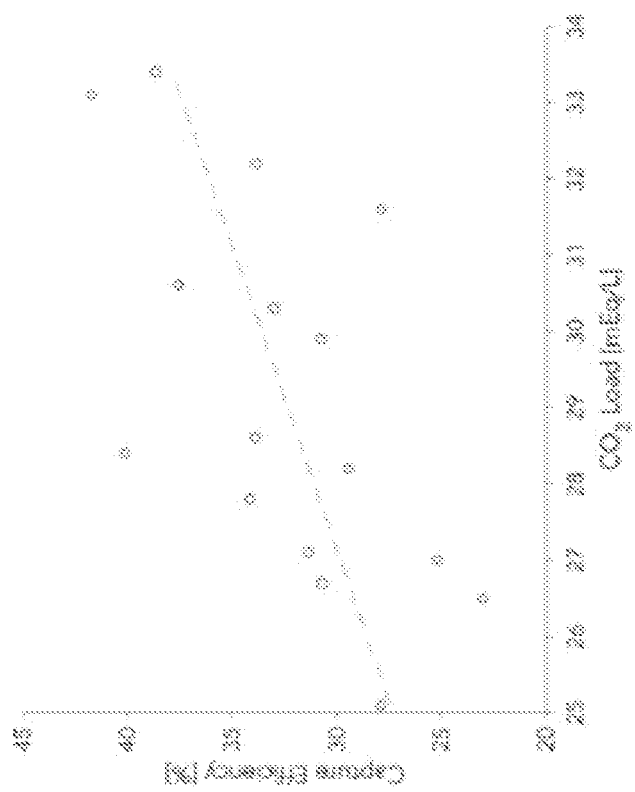
FIG. 15 illustrates efficiency of membrane carbon dioxide capture (%) at different $CO_2$ loads (mEq/L), determined from animal model experiments.
Figure 16:
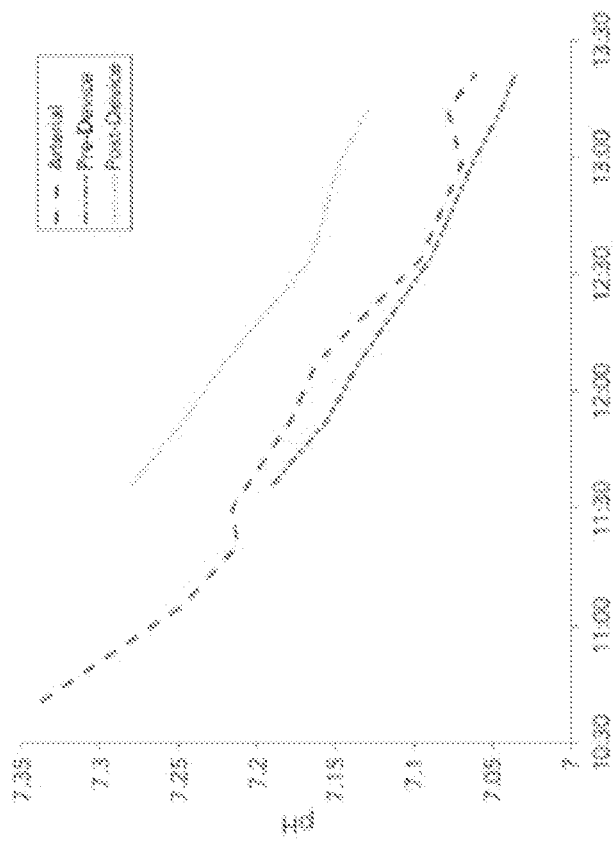
FIG. 16 illustrates pH value changes due to the acute intervention and device function. pH values were measured over a time period from about 10:45 am to about 13:20 pm, with serial measurements in arterial blood, venous blood prior to the treatment, and venous blood after the treatment. It was found that the device operation caused a net increase in pH that helped to counteract the rapid drop induced by the acute intervention. For reference, at time point 13:00, from bottom to top, the curves with circle plot indicators are: pre-device, arterial, and post-device.

An example time course from a single animal is shown in FIG. 14 which shows $CO_2$ capture efficiency in pre-device, post-device, and arterial blood flows, respectively. In the conducted experiments, carbon dioxide load in the animal was consistently increased. The carbon dioxide load began to decrease as the device was activated, which occurred at approximately 11:30 AM, as shown in FIG. 14. This was followed by a rapid decrease in $CO_2$ load in the arterial side, which represents the composite effect from the device. Pre-device measurements are venous measurements drawn from the flow prior to device conditioning and post-device are venous measurements drawn from the flow after device conditioning. Membrane capture efficiency is captured from these differences in the same way as done in benchtop tests. Membrane efficiency is weakly associated with carbon dioxide loads. This relationship is shown with composite data from all animals shown in FIG. 15. The values were similar to those predicted based on benchtop tests. The pH balance was also evaluated pre- and post-device, as shown in FIG. 16. Due to the nature of the intervention to induce the disease state, there was a consistent drop in pH (acidemia) that was independent of the device operation. Measures of pH pre- and post-device blood showed that there was only an increase in pH (more alkaline) from the device that was caused by the hybrid removal of constituent components. This prevented the increased drop in pH that would have occurred with isolated bicarbonate removal. Overall the device tempered the drop in pH induced by the highly acute intervention. This shows the capability to both improve pH and rapidly reduce overall $CO_2$ load.

Figure 17:
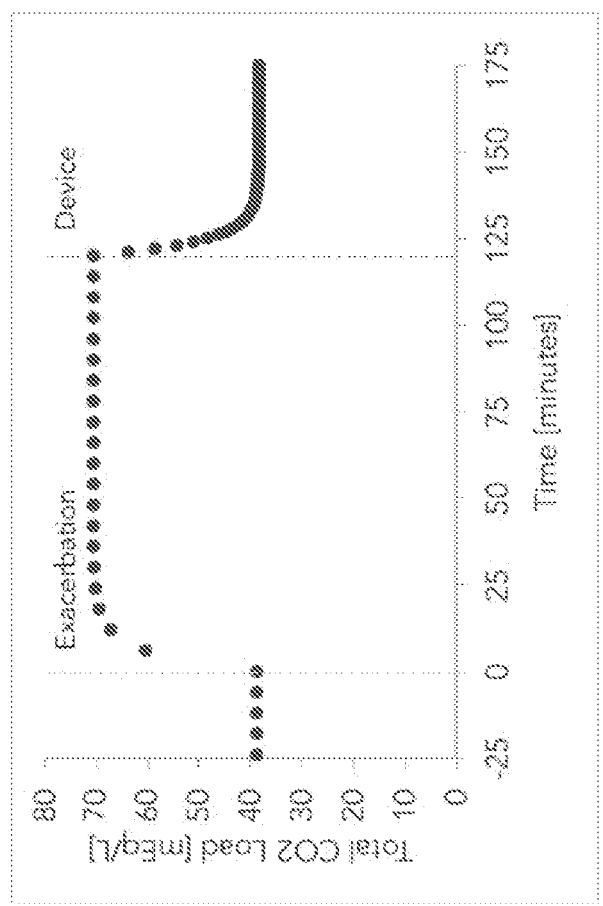
FIG. 17 illustrates performance of a computational model of a hypothetical patient undergoing exacerbation triggered by loss of ~50% of lung function. The therapy using a device in accordance with the described techniques, using animal-model experiments results, was able to return the patient's blood carbon dioxide content to its physiologic baseline in 20 minutes.

Using data from these animal trials, device performance models were put in a kinetic model of a hypothetical subject with a linear fit for membrane efficiency that was capped with a maximum value found in the model (~38%). This assumption is conservative because it results in an underestimation of device performance. It was found that, the use of 250 mL of flow through the device, allowed a subject undergoing an exacerbation due to loss of ~50% lung capacity to return to baseline levels of $CO_2$ load in 20 minutes, as shown in FIG. 17.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features. Further, the term "substantially" means that the recited characteristic, parameter, or value need not be achieved exactly, but that deviations or variations including, for example, tolerances, measurement error, measurement accuracy limitations, manufacturing tolerances and other factors known to those of skill in the art, can occur in amounts that do not preclude the effect that characteristic, parameter, or value was intended to provide. In the description presented herein, the term "about" or "approximately" refers to a range of values within plus or minus 10% of the specified number.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

What is claimed is:

1. An extracorporeal system for removing carbon dioxide from a fluid, the system comprising:
   a cartridge body having a cavity, a longitudinal axis extending between first and second ends of the body, a fluid inlet adjacent to the first end, and a fluid outlet adjacent to the second end;
   a first membrane component disposed within the cavity and configured to remove gaseous carbon dioxide from the fluid passing from the fluid inlet in a first direction towards the fluid outlet;
   a second membrane component disposed within the cavity and configured to remove bicarbonate from the fluid passing between the fluid inlet and the fluid outlet;
   a first inlet in fluid communication with the first membrane component and configured to deliver a sweep gas to the first membrane component such that the sweep gas is passed through the first membrane component in a second direction;
a first outlet in fluid communication with the first membrane component and configured to receive the sweep gas passed through the first membrane component;
a second inlet in fluid communication with the second membrane component and configured to deliver a dialysate to the second membrane component such that the dialysate is passed through the second membrane component in a third direction; and
a second outlet in fluid communication with the second membrane component and configured to receive the dialysate passed through the second membrane component; and
a third membrane component positioned such that the fluid is brought in contact with the third membrane component after passage through the first membrane component and the second membrane component, wherein the third membrane provides an interface between the fluid and a reconditioning fluid, the reconditioning fluid having a composition configured to regulate an ionic composition and acidity of the fluid.

2. The system of claim 1, wherein the fluid comprises blood.

3. The system of claim 1, wherein the fluid inlet receives the fluid at a flow rate in a range from about 0 mL/min to about 350 mL/min.

4. The system of claim 2, wherein at least one of the second and third directions is substantially parallel to the first direction.

5. The system of claim 1, wherein at least one of the reconditioning fluid and the dialysate comprises at least one biocompatible organic base.

6. The system of claim 5, wherein the biocompatible organic base comprises monoethanolamine (MEA).

7. The system of claim 1, wherein the first membrane component comprises a first plurality of fibers extending between the first and second ends and configured to receive the sweep gas passing therethrough, and the second membrane component comprises a second plurality of fibers extending between the first and second ends and configured to receive the dialysate passing therethrough.

8. The system of claim 7, wherein the first plurality of fibers are intermingled with the second plurality of fibers or the first plurality of fibers are substantially parallel to the second plurality of fibers.

9. The system of claim 7, wherein the first plurality of fibers are disposed in a first area of the cavity of the cartridge body and the second plurality of fibers are disposed in a second area of the cavity of the cartridge body, the second area being different than the first area.

10. The system of claim 7, wherein the first plurality of fibers and the second plurality of fibers are disposed at an angle to the longitudinal axis of the cartridge body, and wherein the first plurality of fibers are disposed at an angle with respect to the second plurality of fibers.

11. The system of claim 1, further comprising a controller having circuitry configured to acquire measurements of at least one parameter characterizing a state of at least one of the fluid, the dialysate, and the sweep gas as the fluid passes through the cartridge body, and to control, in response to the acquired measurements, at least one of a flow rate of the fluid, a flow rate of the dialysate, and a content of the dialysate.

12. The system of claim 11, wherein the at least one parameter comprises one or more of electrolyte content of the fluid, pH values of the fluid, and a flow rate of the sweep gas and a content of the sweep gas, and wherein
the system comprises at least one electrolyte sensor configured to measure the electrolyte content as the fluid passes through the cartridge body, and/or
the system comprises at least one pH meter configured to acquire the pH values of the fluid as the fluid passes through the cartridge body.

13. The system of claim 1, wherein the system is adapted for use with a kidney dialysis system.

14. The system of claim 1, wherein at least one of the reconditioning fluid and the dialysate comprises a liquid composition suitable for counter transport to maintain electrical neutrality, and/or the reconditioning fluid and/or the dialysate comprises a liquid composition suitable for unidirectional co-transport to maintain electrical neutrality.

15. The system of claim 1, wherein at least one of the reconditioning fluid and the dialysate comprises zero bicarbonate and at least one of sodium, chloride, potassium, calcium, phosphate, sulfate, magnesium, and glucose.

16. A method for removing gaseous carbon dioxide and bicarbonate from fluids, the method comprising:
removing a fluid from a patient via a cannula in fluid communication with the patient's body;
causing the fluid to enter an extracorporeal housing comprising a first membrane component, a second membrane component, and a third membrane component such that the fluid is placed in contact with exterior surfaces of at least one of the first, second, and third membrane components;
passing a sweep gas through the first membrane component to cause gaseous carbon dioxide to transfer from the fluid into the sweep gas;
passing a dialysate through the second membrane component to cause bicarbonate to transfer from the fluid into the dialysate;
passing a reconditioning fluid through the third membrane component to cause ionic transfer and pH balancing of the fluid after gaseous carbon dioxide and bicarbonate are removed; and
causing the fluid to exit the housing after the fluid has passed through the housing such that the gaseous carbon dioxide and bicarbonate are removed from the fluid by ionic transfer and acidity balance of the fluid.

17. The method of claim 16, wherein the patient is afflicted with hypercarbic respiratory failure (HRF).

18. The system of claim 1, wherein at least one of the reconditioning fluid and the dialysate comprises a liquid composition suitable for balancing the acidity of the fluid.

* * * * *